United States Patent [19]
Fitzpatrick et al.

[11] Patent Number: 5,710,009
[45] Date of Patent: Jan. 20, 1998

[54] RECEPTOR:RELEASE LIGAND (RELAND) COMPLEXES AND RELEASE ASSAYS USING SAID RELAND AND METHODS AND KITS BASED THEREON

[75] Inventors: Judith Fitzpatrick, Tenafly, N.J.; Regina Lenda, Wesley Hills, N.Y.

[73] Assignee: Serex, Inc., Maywood, N.J.

[21] Appl. No.: 493,420

[22] Filed: Jun. 22, 1995

Related U.S. Application Data

[63] Continuation-in-part of Ser. No. 196,092, filed as PCT/US92/06249 Jul. 29, 1992, published as WO93/03367 Feb. 18, 1993, Pat. No. 5,527,686.

[51] Int. Cl.$^6$ .................................................. G01N 33/535
[52] U.S. Cl. .................. 435/7.9; 435/7.93; 435/6; 435/188; 435/975; 436/512; 436/518; 436/525; 436/534; 436/541; 436/530; 436/808
[58] Field of Search ............... 435/7.2, 7.9, 7.93, 435/6, 183, 188, 975; 436/512, 518, 525, 534, 541, 547, 808, 804, 815, 816, 530

[56] References Cited

U.S. PATENT DOCUMENTS

| | | | |
|---|---|---|---|
| 3,817,837 | 6/1974 | Rubenstein et al. | 435/7.9 |
| 4,069,105 | 1/1978 | Singh | 530/363 |
| 4,318,707 | 3/1982 | Litman et al. | 436/537 |
| 4,323,507 | 4/1982 | Leung et al. | 549/231 |
| 4,341,866 | 7/1982 | Yoshida | 436/7.9 |
| 4,434,236 | 2/1984 | Freytag | 436/512 |
| 4,480,042 | 10/1984 | Craig et al. | 436/533 |
| 4,504,412 | 3/1985 | Khanna | 436/188 |
| 4,551,426 | 11/1985 | Freytag et al. | 435/14 X |
| 4,590,278 | 5/1986 | Edwards, III | 546/281 |
| 4,766,064 | 8/1988 | Williams et al. | 435/6 |
| 4,977,077 | 12/1990 | Ngo et al. | 436/501 X |
| 5,009,998 | 4/1991 | Chow et al. | 435/7.92 |
| 5,137,808 | 8/1992 | Ullman et al. | 435/7.9 |
| 5,164,504 | 11/1992 | Walling et al. | 546/281 |
| 5,177,021 | 1/1993 | Kondo | 436/518 |
| 5,183,740 | 2/1993 | Ligler et al. | 435/7.32 |
| 5,188,939 | 2/1993 | Mangold et al. | 435/7.92 |
| 5,527,686 | 6/1996 | Fitzpatrick et al. | 435/7.9 |

OTHER PUBLICATIONS

Steward et al., "The Importance of Antibody Affinity in the Performance of Immunoassays for Antibody," *Journal of Immunological Methods*, vol. 78, pp. 173–190 (1985).

Schwartz, et al., 1991, "Accuracy of common drug screen tests", American Journal of Emergency Medicine, 9:166–170.

Mouine, et al., 1990, "Methods of theophylline assay and therapeutic monitoring of this drug", Ann. Biol. Clin., 48:287–293.

Gosling, 1990, "A decade of development in immunoassay methodology", Clin. Chem. 36/8:1408–1427.

Schramm, et al., 1990, "Rapid solid–phase immunoassay for 6–Keto Prostaglandin $F_{1\alpha}$ on microplates", Clin. Chem. 36:509–514.

Kauvar, et al., 1990, "Parlog chromatography", Bio Chromatography, 5:22–26.

Prattis, et al., 1990, "Detection of mouse thymic virus (MTLV) antigens in infected thymus by competition immunoassay", Laboratory Animal Science, 40:33–36.

Barnard, et al., 1989, "Measurement of Estrone–3–glucuroride in Urine by Rapid, homogeneous time–resolved fluoroimmunoassay", Clin. Chem., 35:555–559.

Castro, et al., 1988, "Fluorescence polarization immunoassay for the determination of nicotine", Biochemical Archives, 4:77–84.

Fitzpatrick, 1986, "Purification of antisera to beta human chorionic gonadotropin by a low–affinity chromatography technqiue", Clin. Chem., 32:1157.

Hinds, et al., 1985, "Ligand displacement immunoassay—demonstration of its use for the measurement of serum phenobarbital and phenytoin", Clinica Chimca Acta, 149:105–115.

Hinds, et al., 1984, "Ligand displacement immunoassay: a novel enzyme immunoassay demonstrated for measuring theophylline in serum", Clin. Chem., 30:1174–1178.

Kulpmann, et al., 1984, "Determination of total and free phenytoin in serum by non–isotopic immunoassays and gas chromatography", J. Clin. Chem. Clin. Biochem., 22:773–779.

Hankins, et al., 1970, "Pyrrolidine–substituted nicotine analogs: synthesis and pharmacology", Journal of Pharmaceutical Sciences, 59:342–343.

*Primary Examiner*—James C. Housel
*Assistant Examiner*—Susan C. Wolski
*Attorney, Agent, or Firm*—Arnall Golden & Gregory, LLP

[57] ABSTRACT

Assays using receptor:reland complexes capable of releasing the reland in the presence of an analyte are described, wherein the reland does not detectably compete with analyte for binding to the receptor. The dissociation constant of the reland and the receptor is such that no appreciable release of reland occurs in the absence of analyte for the receptor. In a preferred embodiment, the association constant of the monomeric reland and the receptor is less than or equal to about $10^5$M, preferably $10^3$ to $10^5$M, most preferably 1% or less of the association constant of the analyte and receptor. In a preferred embodiment, the reland is labelled and the amount of analyte bound to the receptor is determined from the amount of labelled reland which is released.

23 Claims, 8 Drawing Sheets

% Difference Between Detection of HbAo and HbGlc

RECEPTOR:RELEASE LIGAND (RELAND) COMPLEXES AND RELEASE ASSAYS USING SAID RELAND AND METHODS AND KITS BASED THEREON

RELATED APPLICATIONS

The present application is a continuation-in-part of U.S. application Ser. No. 08/196,092, filed Feb. 17, 1994, now U.S. Pat. No. 5,527,686 which is a National Stage application of International Patent Application No. PCT/US92/06249, filed Jul. 29, 1992, published as WO93/03367 Feb. 18, 1993, each of which is incorporated herein by reference in its entirety.

FIELD OF THE INVENTION

The present invention relates to novel, stable receptor:release ligand (termed herein "reland" as defined below) complexes, methods for producing them and methods for using them. It further relates to methods for determining the presence of an analyte in a sample. More particularly, it relates to homogeneous liquid phase and heterogeneous liquid phase/solid-phase release assays that are highly specific and sensitive. The methods and kits of the invention greatly increase the sensitivity, specificity, and dynamic range of assays for analytes and decrease the time and complexity of such assays.

BACKGROUND OF THE INVENTION

Immunoassays utilize the specific binding capabilities of antibodies or antigens to detect the presence of target molecules in a sample. Although the general principle is applicable to a broad range of problems, major commercial interest has centered on medical diagnostic applications for a wide variety of analytes in biological fluids such as blood, saliva, and urine.

Several types of immunoassays, useful for distinct applications, already exist. Each such assay type requires a way of distinguishing whether binding sites on an antibody are occupied or free. Typically, this is accomplished by means of a label such as an atom, molecule, enzyme or particle attached permanently to either the antibody or to the analyte or an analog of the analyte.

Sensitivity and specificity are key parameters of an immunoassay. Specificity relates primarily to the antigen binding site of the antibody, which is inherent to selection of variable region gene segments and is independent of the assay configuration. Sensitivity relates primarily to the affinity of the antibody for its ligand and to the inherent detectability of the label. For example, radioisotopes, used for radioimmunoassay, can be detected at significantly lower concentrations than fluorescent molecules. Enzyme labels are detectable at concentrations similar to fluorescent labels. When substrates that produce fluorescent or chemiluminescent products are used with enzyme labels, the sensitivity of resulting immunoassays is comparable or greater than with radioisotope labels.

To date, immunoassays for diagnostics have fallen into two basic categories: sandwich immunoassays, which directly measure the presence of an analyte by "capturing" it between two antibodies, and competitive immunoassays, in which analyte competes with a labeled ligand for binding to the antibody. These assay techniques have drawbacks, however. The sandwich immunoassay requires that the analyte be large enough to accommodate binding to two antibodies, and is thus more suitable for larger analytes, such as proteins. Competitive assays, in which an analyte and ligand have comparable binding affinities for the antibody, are driven primarily by mass action, and therefore lack sensitivity or dynamic range, or both. Where the affinity of analyte and ligand for antibody are significantly different, the assay becomes overly sensitive to matrix effects, as the lower affinity binding interaction is more influenced by variables such as temperature, pH, salt concentration, and the presence of denaturing agents (e.g., in urine).

Many conventional assay techniques are considered competitive in that the analyte and labeled component have comparable affinities for the antibody binding site. One example of such a competitive method is found in U.S. Pat. No. 3,817,837 to Rubenstein and Ullman which describes a technique in which analyte and enzyme:ligand conjugate compete for antibody binding sites. Since binding of the antibody to the enzyme:ligand conjugate alters its enzymatic activity, the concentration of analyte present can be estimated by measuring the rate at which such a mixture converts substrate to product.

A variation on competitive assays is the dissociative assay which utilizes a preformed antibody:ligand complex with a high dissociation constant, and in which competition occurs after the dissociation of the ligand from the antibody. This type of assay has not been reported to have any significant advantages over conventional competitive assays. Current dissociative assays such as some fluorescence polarization assays do not provide a stable, preformed immune complex, but require addition of ligand to antibody several minutes before addition of analyte resulting in increased complexity.

Immunoassays can be further characterized as homogeneous or heterogeneous. In a heterogeneous method, the label is equally detectable in bound and unbound states. To obtain any meaningful assay results physical separation of the bound from unbound antibody is required. A common strategy for accomplishing this separation entails associating the label to a solid phase which can be physically separated from the liquid phase prior to the detection step. A typical heterogeneous assay is the CotiTraq$^R$ Elisa Kit for the detection of cotinine in urine from Serex, Inc., Maywood, N.J.

In a homogeneous method, the detectable property of the label is inherently different depending on whether it is bound or unbound to antibody. In its bound state, the label will have greater or lesser signal intensity. Usually, binding of antibody to the labeled ligand causes a decrease in signal intensity, e.g., when the label is an enzyme. Typical products in this category include the EMIT$^R$ line of enzyme immunoassays from Syva Company, Palo Alto, Calif., and the TDX line of fluorescence polarization immunoassays from Abbott Diagnostics, Chicago, Ill.

Two further characteristics of immunoassays are particularly noteworthy. These are the minimal concentration of analyte that can be detected, and the dynamic range of detection. The dynamic range is the range of analyte concentrations over which signal from a label changes from zero to maximum. The order in which the sample, the antibody, and a labeled component are combined can significantly affect both of these key parameters by affecting the degree of binding of the labeled component, which in turn affects detection of the label.

In certain known assay methods, the antibody and the analyte are combined prior to addition of the labeled component. In others, the analyte and labeled component are combined prior to addition of the antibody. Each of these cases requires providing two separate reagents that are combined with the sample containing the analyte. The need for two such separate reagents can be inconvenient and result in a more cumbersome, complex method. Moreover, because precise volumetric measurement of each reagent is critical to good assay performance, the necessity of two measuring steps can cause errors which may lead to distorted results.

One method of improving assay precision and thereby enhancing assay sensitivity is to provide a premixed complex of the antibody and labeled component. This is problematic, however, because the binding reaction is generally found to be virtually irreversible under most test conditions. Thus, when a complex of the preformed labeled analyte and antibody are combined with a solution containing the analyte, no appreciable displacement of bound label occurs in a meaningful time frame (minutes).

SUMMARY OF THE INVENTION

Novel receptor:reland complexes are provided by the invention. The term reland is a coined word meaning release ligand. The present invention is based on the discovery that a reland selected in accordance with this invention can be made to complex with a receptor and to impart to the receptor:reland complex properties not described in the prior art. The novel complexes are stable, i.e. virtually irreversible in the absence of analyte, but surprisingly when brought into contact with analyte are virtually completely unstable resulting in the rapid release of reland. Release of the reland from the stable receptor:reland complex in the presence of analyte is the essence of the invention. The reland may be in a monomeric or multimeric form as will be described more fully herein below.

The present invention also relates to methodology that employs the novel, stable, complexes of the reland with a receptor for an analyte wherein the receptor:reland complex is capable of releasing the reland in the presence of an analyte. The reland, appropriately labeled, is detectable, thereby positively indicating the presence of analyte in a test sample when the method is used in a diagnostic assay format. Methods for designing, preparing, using, and stabilizing such complexes are provided. The methodology is applicable both to homogeneous assays and heterogeneous assays for analytes encompassing a broad range of types and sizes. The assays and complexes of the present invention overcome the disadvantages and drawbacks of the diagnostic assays of the prior art as for example by detecting the presence of an analyte in a shorter time with greater sensitivity and a larger dynamic range than has heretofore been possible in a single assay design.

The invention is also applicable to both in vivo diagnostic assays and therapeutic methods of treatment. For example, in a broad aspect, the present invention provides novel complexes useful in novel methods for reaching and reacting with a specific site in the body. The method comprises delivering a receptor:reland complex to a site in the body and detecting binding of the receptor to the site following release of the reland from the complex. In this case, detection is facilitated by the incorporation of a "label", or detection system in whole or in part, into the receptor or therapeutic agent.

The invention advantageously provides kits comprising the preformed receptor:reland complex, or each agent separately, for use in the heterogenous and homogeneous assay methods taught herein or in the in vivo diagnostic or therapeutic methods of treatment. The receptor:reland complex may be formed prior to contacting the sample with the complex by incubation of the receptor with the reland for an appropriate period of time.

An essential aspect of the invention is the choice of reland to form complexes having properties which are substantially different from the properties of the ligand:receptor complexes described in the prior art competitive or dissociative assays. Since the formation of a suitable receptor:reland complex depends upon the characteristics of the reland, it is appropriate at this point to present some of these characteristics. Further and more specific details will be presented infra.

The reland is structurally related to the analyte and in monomeric form demonstrates less than 1% cross-reactivity of binding to the receptor, an effect which would appear to be inconsistent with the ability to form a stable complex. In direct contrast to the assays and complexes of the prior art, the reland does not detectably compete with analyte for binding to the receptor. In preparing the complex, we have found that the monomeric reland associates with the receptor only at high concentrations of reland (lower concentrations may be used when the reland is presented as a multimer) and it does so with slow kinetics and only in the absence of analyte. The reland does not detectably affect the essentially complete binding of analyte to the receptor nor does it bind to the receptor in the presence of analyte. In a specific aspect, the association constant of the monomeric reland and the receptor is less than or equal to about $10^5$M, preferably $10^3$ to $10^5$M and most preferably around $10^4$M. When complexed to the receptor as a multimer, as for example, when the reland is a dimer, trimer or higher -mer, or when conjugated to a carrier such as a peptide (still a multimer as used herein), the association constant is dramatically increased. It is not preferred to exceed a total molecular weight for the reland of greater than 5,000 Daltons if optimum releasability is an objective, however. This is for the reason that larger molecule sizes tend to favor the formation of irreversible complexes with the receptor and favor higher cross-reactivity with the analyte. However, when the complex is formed at or near the time of performance of the assay, so that irreversability of the complex is not a factor, the higher molecular weight multimers such as are obtained from BSA, BCG, G6PH, and others lead to suitably releasable complexes provided the cross-reactivity parameters are acceptable.

In a highly preferred aspect of the invention, the molecular weight of the reland is less than 5000 Daltons, and more preferably, less than 2000 Daltons. The molecular weight of the reland for purposes of the invention includes the epitope that directs binding with the receptor, as well as any linkers, labels, or ancillary structures of the reland. By providing a reland of small size, the present invention helps ensure that irreversible complex formation between the reland and the receptor is avoided. This is especially important because it limits the supply of a preformed complex in a kit. The complex, when prepared at the site or just before use, nevertheless acts suitably as a releasable complex.

Theoretically, in designing the complex, one could choose to modify either the reland or the binding site of the receptor. But in practice, it is much more practicable to modify the reland. There is a wide variety of receptors available for use in the invention as will be described infra.

The diagnostic methods of the present invention using the novel complexes provide surprisingly greater sensitivity, specificity, accuracy and range of detection than conventional association assays or competitive dissociation assays such as described in Freytag U.S. Pat. No. 4,551,426.

Analytes may be any antigen or target molecule as described herein including therapeutic drugs and metabolites thereof, illicit drugs and metabolites thereof, steroids, and peptide hormones, hormones, e.g., insulin, viral antigens, bacterial antigens, serum proteins, antibodies, toxins, pesticides, environmental products, cancer antigens, genetic markers, or any antigen of interest where detection of presence (or absence) of the analyte in a rapid, specific, sensitive assay is desired.

DEFINITIONS

Analyte—molecule of interest in an assay or at a site in the body; also the target of the receptor.

Reland—a word coined from the term "release ligand" which describes the release properties of the ligand when complexed; a molecule capable of binding to a receptor and which demonstrates the following properties:

- the reland may be monomeric or may be in multimeric form such as dimer, trimer, 4-, 5-, 6-mer or higher -mer of the monomeric molecule; "multimer" also includes conjugations of the reland to a carrier such as peptides, sugars, polymers, and the like;
- the dissociation constant of reland and the receptor is such that no appreciable release of reland occurs in the absence of analyte for the receptor;
- the dissociation constant of the reland-receptor complex is extremely low, such that analyte induced release of the reland is not dependent upon or related to the dissociation rate of the stable complex;
- the reland is structurally related to the analyte in monomeric form, but has less than 1% cross reactivity with the receptor, and more preferably, does not detectably cross-react or compete with analyte for binding to the receptor;
- release of the reland from the receptor:reland complex is induced by the analyte;
- the reland associates with the receptor with slow kinetics in the absence of analyte;
- in preforming the complex, there is no appreciable binding of monomeric reland to the receptor until the concentration of reland is about $10^{-5}$M, preferably $10^{-3}$ to $10^{-4}$M or at lower concentrations, e.g. $10^{-5}$ and lower ($10^{-6}$ to $10^{-8}$ or larger) when the reland is in the form of multimers. Receptor concentrations are usually within the range of from $10^{-6}$ to $10^{-10}$M, but values outside that range may be employed;
- the monomer (or multimer) reland binds to the receptor with substantially lower affinity than that of analyte binding to the receptor, but the receptor:reland complex has a dissociation constant similar to that of receptor:analyte complexes.

Receptor—a specific binding partner of the analyte; a molecule capable of specifically binding to analyte or to reland as described herein. In each case, a stable complex is formed, but the association constant of the analyte is higher than that for reland. A preferred receptor is an antibody, but other specific binding partners, as described hereinbelow are also contemplated by the invention.

BRIEF DESCRIPTION OF THE DRAWINGS

FIG. 8A, 40 micrograms/ml; FIG. 8B, 1 microgram/ml; and FIG. 8C, 0.25 micrograms/ml.

DETAILED DESCRIPTION OF THE INVENTION

Figure 1A:
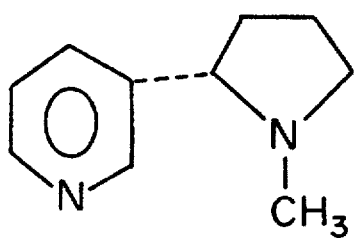
FIG. 1 Molecular formulae. (A) nicotine, (B) cotinine, (C) N-isopropyl-4-carboxyl-norcotinine and (D) N-propyl-4-carboxyl-norcotinine.
Figure 1B:
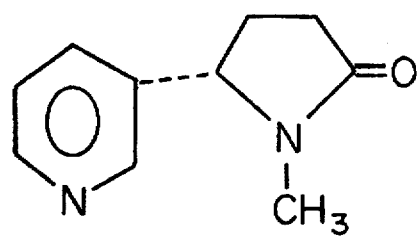

In accordance with the present invention applied to in vitro diagnostics, there is provided a method for detecting the presence of analyte in a sample, using novel receptor-:reland complexes and kits, therefor. A test sample can be any fluid suspected of containing the target analyte, such as milk, water, urine, blood, serum, saliva, bodily exudate, etc. and liquids derived from solid materials of interest such as soil, foods, chemicals, body tissue, and the like. The release assay method of the invention involves contacting a test sample with a receptor:reland complex and, if analyte is present, detecting release of the reland (or the released receptor) from the complex or detecting the binding of the receptor to the analyte in appropriate cases.

It is believed that the release reaction occurs when the analyte contacts the receptor:reland complex forming a putative tri-molecular complex. The presence of analyte with an association constant with receptor of greater than or equal to $10^8$M (e.g. $10^9$, etc.) induces a change in the receptor:reland complex that changes the dissociation constant of the complex allowing the release of the reland. This interaction of analyte with receptor may be at the binding site of the reland or at an allosteric binding site. After release of reland, the complex of analyte and receptor is not detectably affected by the presence of free reland. Either reland or receptor can be detected after release from their initial complex to indicate the presence of analyte in the sample. The assay method of the invention may be performed in either homogeneous or heterogeneous formats. Specific details of each format are provided infra.

A release assay of the present invention allows preparation of a complex in which the binding site or binding sites on the receptor and reland are present in approximately equal concentration, i.e., quantitative complex formation, although this is not essential. Having each element present in equal concentration enhances sensitivity, because if the receptor is present in excess, it can bind analyte without releasing reland from the complex.

In order to achieve a receptor:reland complex in which the number of binding sites of each element is present in substantially equimolar amounts, the receptor and reland are incubated for at least one hour prior to exposure to sample, although shorter incubation times are possible if either reagent is present in a vast excess over the other. Preferably the incubation time is greater than about twelve hours. A long incubation time allows formation of the most stable complexes during repeated release and binding reactions when one element, either receptor or reland, is present in excess. After this low affinity binding reaction reaches equilibrium, the receptor:reland complex, now stable following a long-term incubation, is isolated from the excess reagent (either reland or receptor). Isolation of the complex may be accomplished by precipitation, size exclusion chromatography, density gradient centrifugation, microfiltration, or other techniques for separating complexes from their components. Alternatively, to avoid a separation step, the receptor and reland may be mixed in equal binding site concentrations or at slight excess (about 1-to 2-fold) of reland and incubated for a time which depends upon concentration of reland to allow substantially quantitative binding as stable complexes. For example, (FIG. 8C) at reland concentrations of 0.25 ug/ml, an incubation of a week or more was required. Formation of the reagent:reland complex is discussed more fully, infra. To overcome the cost of providing reland label at high concentration and subsequently separating bound and free, the reland may be polymerized to multimer form. In such form, binding will go to completion at stoichiometric levels of receptor and reland.

The methods of the present invention are based on the discovery that release of reland from a complex of receptor and reland in the presence of analyte is induced by the analyte. The released reland does not reassociate with the receptor and, therefore, does not compete with the analyte for binding sites on the receptor. It is thought that this result is occasioned at least in part as a consequence of the association constant of binding for the reland to receptor which for the monomeric reland is about $10^5$M and preferably $10^4$ to $10^3$M.

The release of reland from the receptor:reland complex in the presence of analyte is termed herein the release reaction. It is significant to note that the release is virtually complete (that is, essentially all reland is released) within seconds to minutes after the analyte contacts the complex. The free reland does not reassociate with receptor within the time frame of the analysis, test, or method. While it has been postulated that the corollary to reland release is that the free receptor combines with the analyte to form a stable complex, it is not necessary to the invention for that to occur. The amount of reland released is directly proportional to the amount of analyte encountered by the reland:receptor complex and, thus, a measure of the amount of released reland is a measure of the amount of analyte present.

Although not intending to be limited by any particular hypothesis for a mechanism of the release reaction, it is believed, based on the fast kinetics of the release reaction despite the stability of the receptor:reland complex, and the resultant non-dependence of reland release on the dissociation rate of the receptor:reland complex, that a tri-molecular complex between receptor, analyte, and reland forms when analyte is present. Due to the high affinity of the analyte for the receptor, and the relative instability of the tri-molecular complex, the reland is released, allowing the analyte to complex with the receptor. Since the reland does not detectably compete with analyte for binding to the receptor, the complex of analyte and receptor is not noticeably affected by the presence of the reland. This hypothesis is also consistent with the existence of a double binding site on the receptor.

Preferably the association constant of binding of receptor to monomeric reland will be no more than about 1%, and more preferably not more than about 0.2%, of the association constant of binding of receptor to analyte. This can be observed qualitatively as relative binding, e.g., by apparent activity in an assay.

Since the release reaction depends on a high affinity association of receptor and analyte, it is sensitive and specific. That is, receptor will bind low concentrations of analyte. Dependence of the release reaction on the differential affinity binding further increases specificity. Receptor will not dissociate and bind cross-reactive analogs of the analyte unless the binding constant is much higher than the binding constant of receptor and reland.

One of the significant advantages of the relationship between analyte and reland according to present invention is that the effective ratio of analyte to reland to induce the release reaction is less than 100:1, preferably less than 10:1, and more preferably about 1:1. In fact, a 1:1 ratio induces virtually complete and stoichiometric release. This characteristic of the assays of the invention is significantly different from the prior art dissociation methods, in which the ratio of analyte needed to release analog of analyte (which is cross-reactive with the analyte) is substantially greater than 100:1, since it is dependent on the Kd of the receptor ligand.

It is important to emphasize that an effective portion of the receptor:reland complex must release in the presence of analyte, and very little must release in the absence of analyte, or the background "noise" in the system will be a considerable factor. For example, if only 1% of the receptor:reland complex were to release, 99% of the system would be unaffected. If the standard deviation of measurement were 1% (equivalent to 99±1%), which represents an excellent coefficient of variation in immunoassay systems, then the effect of 1% release would be 1%±1%, nullifying any significance. The present assay provides for significant dissociation of receptor:reland complex, i.e., release above the baseline levels.

The stoichiometric release of the reland also provides the opportunity for a broad concentration range over which analytes can be detected. In the prior art competitive systems, the assay design requires use of limiting amounts of ligand in order to detect small amounts of analyte in a sample. Such a configuration would be swamped out by a large amount of analyte however. Conversely, where high levels of analyte are expected, greater amounts of the analyte analog are required. Under these conditions, the baseline dissociation would be about equal to, or even exceed, dissociation in the presence of a small amount of analyte. Accordingly, the instant invention overcomes these deficiencies of the prior art by providing the preformed receptor:reland complex, stable in the absence of analyte, yet potentially quantitatively releasable in the presence of analyte.

The amount of reland released, while potentially quantitive, can be affected by the system. For example, in a heterogeneous system, when a solid phase complex of horseradish peroxidase-labeled antibody to cotinine as receptor and isopropylnorcotinine as reland, linked to a carrier protein (e.g., glucose-6-phosphate dehydrogenase) to facilitate binding to the solid phase, is reacted with sample, 5–10% of total antibody is released by analyte. The exact percentage is difficult to ascertain since enzyme activity on a solid phase is known to be less than that of enzyme in liquid phase. In a homogeneous release assay, using the same reagents, the sample containing cotinine induces 100% reversal of enzyme inhibition, which indicates 100% release. This indicates that lower release seen in the solid phase system, is a function of the system, not of the reland:antibody complex.

Other advantages of the present invention can be readily appreciated by those of ordinary skill in the art. The release reaction is relatively instantaneous, generally under 5 minutes to end point. The diffusion of the reagents is a controlling factor in the time needed for the assay. Thus, the times may be shortened by increasing the concentration of reagents. Most advantageously, the release reaction does not require a highly sensitive detection system. This means that the present invention provides for simple assays, using low sensitivity detectable compounds such as cofactors, dyes, and the like, rather than high sensitivity fluorophores, and thus avoids the need for a complicated—and expensive—detection apparatus as required in prior art competitive dissociation assays.

The Receptor:Reland Complex

Figure 8A:
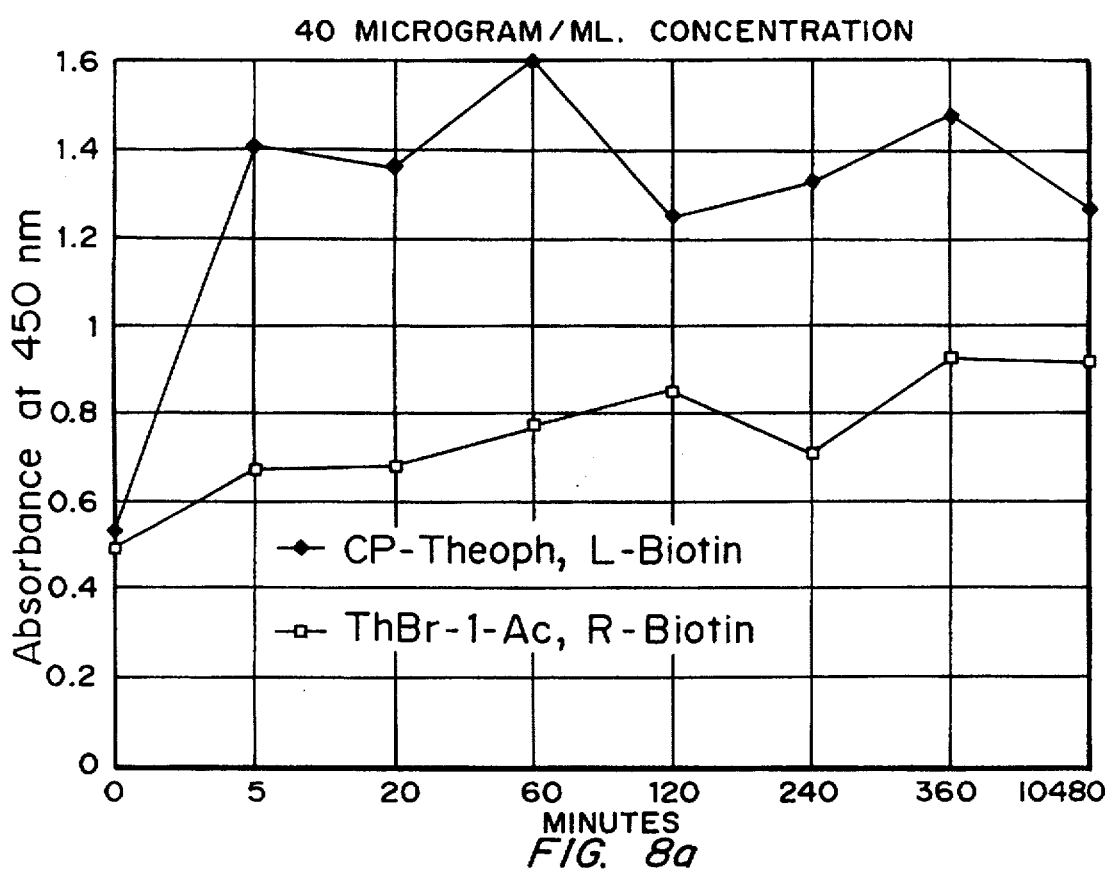
FIGS. 8A, 8B, and 8C Kinetics of monoclonal anti-theophylline binding to theophylline-ligand conjugated to biotin (carboxypropyl-dimethylxanthine-biotin) and theophylline reland-biotin (theobromine-1-acetate-biotin), as a function of concentration.
Figure 8B:
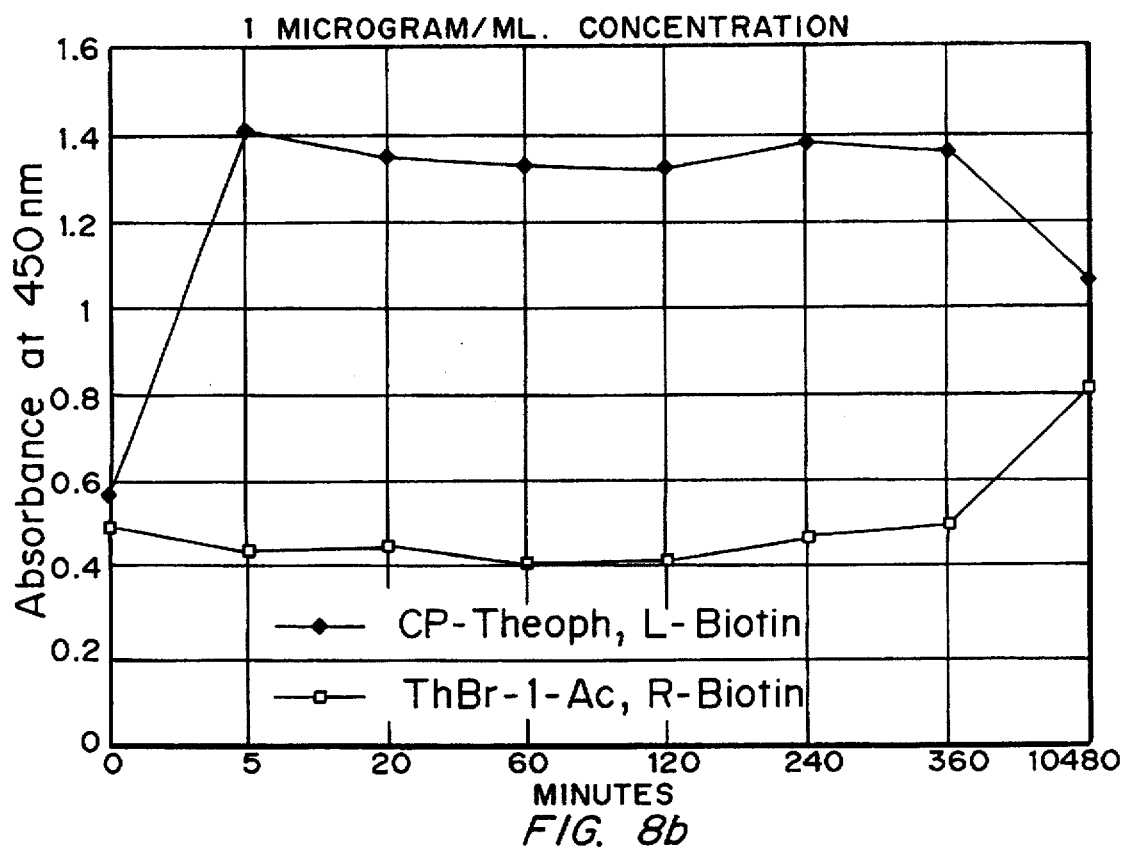
Figure 8C:
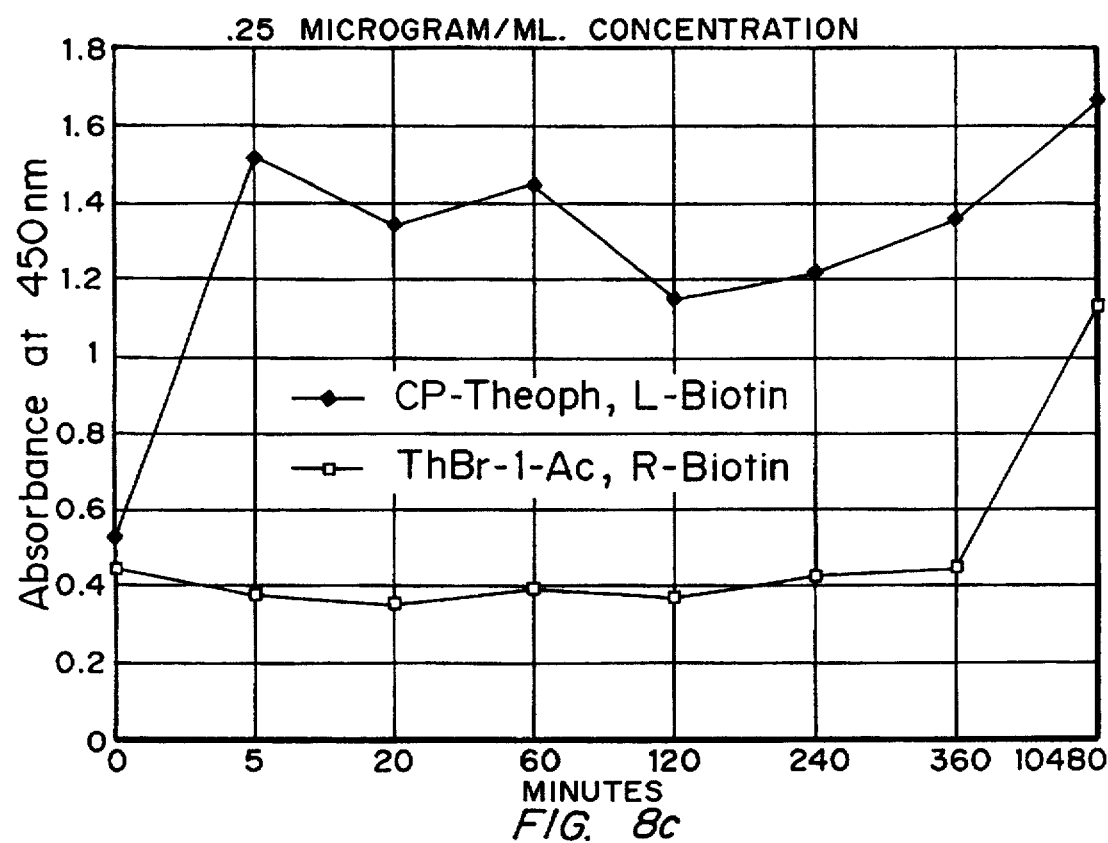

An effective release assay requires the use of a stable receptor:reland complex. This complex forms more slowly than conventional complexes, e.g., receptor: analyte, or antibody:antigen complexes, etc. (FIG. 8A, 8b, 8C). This complex is prepared in an aqueous liquid medium via incubation of the reland and the receptor for a time which depends on the concentration of reagents. At higher molar concentrations, shorter times are required. Release of the complex occurs readily during initial receptor:reland complex formation. After a suitable incubation period, however, usually greater than one hour, and more often greater than 12 hours, the receptor:reland complex becomes stable. Usually, temperatures of 4 degrees C. to 40 degrees C. would be suitable with 4 degrees to room temperature being preferable.

The stability of the complex is in part a function of the design of the reland and the incubation time of reland and receptor. The appropriate incubation time is readily determined for each receptor and reland combination. Generally, however, the receptor and reland should be incubated at least one hour, and preferably longer than 12 hours, prior to exposure to analyte.

Under appropriate conditions, e.g., the presence of salts such as sodium chloride, or stabilizing agents such as proteins or glucose, or both, the stable receptor:reland complex will remain releasable over a long time period—days, weeks or longer. According to the present invention, a stable receptor:reland complex may be in solution, or it may be dried. A complex formed in the presence of 5% sodium chloride could be used six days after receptor:reland complex was prepared. Proteins, sugars or other known stabilizers may also be used to stabilize a dry receptor:reland complex.

Although the present invention is not bound by any theory or hypothesis, it is believed that formation of a stable receptor:reland complex supports a model of molecular accommodation between the reland and the receptor. The equilibrium of this binding favors a configuration of the complex which stabilizes it, meaning that the effective affinity of the complex may, and probably must be, higher in the mature complex than in the initial complex. This is reflected in a very low dissociation rate of the complex.

According to the invention, the reland is preferably labeled with a detection system, or a part thereof. Alternatively, the label may be incorporated into the receptor. It is also contemplated by the invention to supply a portion of a label system to the reland and to provide the remainder of the label system in the test environment. The two portions combine after release of labeled reland to form the indicator detection system. For example, the reland may be labeled with FAD, which is the portion of glucose oxidase which gives activity to the enzyme. When the FAD-reland is complexed with receptor, the FAD is not readily available to glucose oxidase (called "apoglucose oxidase" or apoGO when FAD is absent). When the FAD.reland is released by contact with appropriate analyte, the FAD easily becomes incorporated into the apoglucose oxidase provided in the test system, activates the same and is detected as a measure of the presence or amount of analyte.

Receptors

One element of the receptor:reland complex is a receptor having one or more binding sites capable of specifically binding to analyte, in which the association constant of binding is high. Preferably, the association constant is greater than $10^8 M$, and more preferably greater than $10^{10} M$. The receptor is also capable of binding to monomeric reland with an association constant of binding relatively low compared to that of the constant for receptor binding to analyte. Suitable receptors for use in release assays of the invention include antibodies or a fragment of the antibody that contains binding sites for analyte and reland, cell surface receptors or a fragment of a cell surface receptor that contains binding sites for analyte and reland, or any other molecule or macromolecule capable of specifically binding to and forming a stable complex with both a reland and an analyte. Antibodies and cell surface receptors are preferred, with antibodies more preferred. Most preferred are antibodies generated to a specific epitope, i.e. a drug or small peptide conjugated to an immunogenic molecule such as a protein, polyamino acid (e.g. polylysine) agarose or other polymeric derivatives. In a preferred embodiment, receptor is generated or selected to be specific for the most unique epitope on the analyte.

In a specific embodiment, infra, in which the receptor is an antibody, the antibody is selected for its specificity for a unique epitope on the analyte, e.g., the glycation site of glycated hemoglobin, or a unique sequence of a protein or polypeptide.

Various procedures known in the art may be used for the production of antibodies to analytes of interest. Such antibodies include but are not limited to polyclonal, monoclonal, chimeric, single chain, Fab fragments and an Fab expression library. For the production of antibodies, various host animals may be immunized by injection with a particular analyte or analyte conjugated to an immunogenic carrier, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to analytes may be prepared by using any technique which provides for the production of antibody molecules by continuous cell lines in culture or in vivo. These include but are not limited to the hybridoma technique originally described by Kohler and Milstein, (Nature, 1975, 256:495–497), the more recent human B-cell hybridoma technique (Kosbor et al., 1983, Immunology Today, 4:72) and the EBV-hybridoma technique (Cole et al., 1985, Monoclonal Antibodies and Cancer Therapy, Alan R. Liss, Inc., pp. 77–96). In an additional embodiment of the invention monoclonal antibodies specific to analytes may be produced in germ-free animals utilizing recent technology (PCT/US90/02545). According to the invention, human antibodies may be used and can be obtained by using human hybridomas (Cote at al., 1983, Proc. Natl. Acad. Sci., 80:2026–2030) or by transforming human B cells with EBV virus in vitro (Cole et al., 1985, in, Monoclonal Antibodies and Cancer Therapy, Alan R. Liss, pp. 77–96). In fact, according to the invention, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Such antibodies are within the scope of this invention.

According to the invention, techniques described for the production of single chain antibodies (U.S. Pat. No. 4,946, 778) can be adapted to produce analyte-specific single chain antibodies. An additional embodiment of the invention utilizes the techniques described for the construction of Fab expression libraries (Huse et al., 1989, Science, 246:1275–1281) to allow rapid and easy identification of monoclonal Fab fragments with the desired specificity to analytes.

Antibody fragments which contain sites specific for analytes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

Alternatively, polyclonal or monoclonal antibody specific for an analyte of interest may be obtained from commercial sources.

Receptors for binding analyte may be purified, e.g., by affinity chromatography. Monoclonal antibody may also be purified by protein A or anti-Ig chromatography. Techniques for purifying polyclonal and monoclonal antibodies are well known in the art. A heterogeneous receptor preparation, such as polyclonal antibody, may also be absorbed with a low concentration (e.g., 1% of the receptor concentration) of reland to remove any receptor capable of binding reland with high affinity.

Reland

In further elucidation of the properties set forth under Definitions, as used herein the term "reland" includes molecules with limited cross-reactivity with analyte for binding to the receptor. The term "reland" is used herein interchangeably with release ligand, as reland is a term coined by the co-inventors hereof to refer to a release ligand. The release ligand or reland binds with the receptor with a low association constant, and does not affect the stability of an analyte:receptor complex. Thus, a reland is structurally related to its cognate analyte to allow for a specific binding interaction, but also includes sufficient structural differences to lower affinity and to preclude formation of irreversibly bound complexes. Accordingly, a reland may be an analog of the analyte, including an epitope of the analyte, a derivative of the analyte, a modified analyte, or an isomer of the analyte. Preferably, the reland differs structurally from analyte in a location at or near the epitope. These differences may include chemical modifications, steric, configurational, conformational, or ionic changes. Preferably, ionic groups are substituted with a neutral polar groups, since ionic interactions are particularly strong, and may interfere with release.

Molecules prepared to structurally mimic the analyte are also analogs for use as relands. Such structural mimics may be, but need not be, of the same chemical nature as the analyte so long as the epitope is chemically similar. Thus, for example, as shown in specific examples, infra, a peptide may be an analog of a protein. Once an analyte/receptor pair for investigation has been chosen, potential relands are selected from analogs of the analyte. Analogs of the analyte may be selected by identifying structures similar to analyte, selecting several with different portions of the molecule having been modified as taught herein and looking at cross-reactivity of such structure in a competitive assay for analytes as previously indicated. The modification may in some circumstances be only simple changes or substitutions in structure, such as one step dissociation or substitution of a single amino acid in a polypeptide chain. From those monomeric compounds with cross-reactivity of less than 1% preferably less than 0.1% and most preferably no cross-reactivity at $10^{-6}M$ concentration, several are selected to screen for their ability to stably bind to the receptor. To evaluate stable binding, a preferred method is to conjugate the potential relands to biotin, immobilize the receptor on an Elisa plate, and test the ability of the reland-biotin to bind to the receptor using horseradish peroxidase conjugate to avidin. Of those exhibiting stable binding, several are selected to determine which is released and is stable over time.

If no analogs are commercially available, derivatives may be prepared by adding or deleting modifying groups to the analyte. Derivatives may also be natural metabolic products of the analyte. One of ordinary skill, having the information presented herein, will readily know how to prepare or identify derivatives of analytes for use in the invention. Changes in molecular structure of the analyte will alter the binding affinity of receptor for reland, or bulky groups may enhance the long-term ability to release reland.

Modified analyte includes analyte conjugated with a steric interfering group. Addition of bulky groups, such as aliphatic, aromatic or cyclic molecules or sugars, or ionic groups, or preferably substitution of non-ionic groups for ionic groups, to an analyte or to a peptide can result in decreased binding affinity for receptor due to steric and/or charge interference. Alternatively, conjugation with a bulky group may cause a conformational change in the epitope of the reland that decreases binding affinity with the receptor. Chemical modifications of organic molecules are well-known in the art and may be used to modify reland. For example, an analyte, cotinine, can be modified by the presence of alkyl groups having up to 6 carbon atoms and most preferably, N-isopropyl or N-propyl groups to provide a preferred reland in an assay for cotinine (FIG. 1).

Isomers of analytes are molecules with the same composition but different configuration. Typically, isomers will have a different configuration at a particular carbon center, e.g., cis versus trans, D versus L. Isomers include diastereomers, which have the opposite configuration at one or more chiral centers, and include enantiomers of analytes. Since biological binding interactions depend on configuration as well as conformation and composition, use of an isomer as reland can result in much lower binding affinity for receptors. Usually a decrease in affinity between isomers alone is not sufficient to create a reland, but an isomer may enhance the effect of other alterations.

Where the analyte is a protein, the reland may be prepared synthesizing peptide analogs of the epitope to which the receptor is specific. Recombinant DNA methods using site directed or other mutagenesis techniques to alter the amino acid sequence of the protein may also be used. These techniques are well known to those skilled in the art (e.g., see Zoller and smith 1984, DNA 3:479–488; Oliphant et al., 1986, Gene 44:177; Hutchinson et al., 1986, Proc. Nat'l. Acad. Sci. U.S.A. 83:710). Polymerase chain reaction (PCR) techniques are preferred for site directed mutagenesis (see Higuchi, 1989, "Using PCR to Engineer DNA," in PCR Technology: Principles and Applications for DNA Amplification, H. Erlich, ed. Stockton Press, Chapter 6, pp. 61–70). Preferably, such a recombinantly expressed protein is fragmented, e.g., by digestion with a peptidase, to yield reland fragments of less than about 5000 Daltons molecular weight most preferably. Most preferably, the reland for a protein can be a peptide with molecular weight of less than 2000 that is prepared synthetically.

Reland may also comprise a linking group. A linking group may be used to conjugate a label to reland, e.g., a bifunctional cross-linking agent to facilitate attachment of a label to the reland where the functional groups of the reland and the label do not admit of direct attachment. An example of a linking group is aminocaproic acid. Also, bulky linking groups may be used to sterically hinder binding of reland to receptor. An example of a bulky linking group is p-aminobenzoic acid. Both linking groups and labels can decrease or increase the association and/or dissociation constant. Therefore, selection of a reland requires evaluation of the total reland including linking group and label.

Relands can be evaluated to show their suitability for use in a release assay. Reland evaluation assays include competition assays, binding enhancement assays, direct assays, and microtiter plate release assays, as well as the contemplated release assay itself. The end point of such assays is to demonstrate that reland can form a stable complex with the receptor, that reland does not detectably affect a complex of analyte and receptor, that analyte induces release of reland from a stable complex of the analyte and the receptor, that reland does not significantly induce release of a stable complex of reland and receptor, that reland does not significantly, and preferably does not detectably, compete with analyte for binding to the receptor. These characteristics of a reland can be shown quantitatively, by measuring percentage of release, affinity constants, and the like, or qualitatively, by measuring detectable release and relative binding activities.

Competitive assays useful for evaluating potential relands can be run in an ELISA format, but any competitive assay technique may be used. For example, a reland is much less effective than analyte for inhibiting binding of receptor to analyte on a solid phase. A molecule that is a poor competitive inhibitor relative to analyte can be a good choice for use as a reland.

A low concentration of a suitable reland may actually appear to enhance binding of receptor to analyte in a competitive assay. Thus in a competition type assay increased absolute signal in the presence of a low concentration of the reland candidate indicates that the candidate may be a suitable reland (See FIG. 10).

When a direct assay is used to evaluate a potential reland, binding of receptor and reland is compared to binding of receptor and analyte. An ELISA format is well-suited for this type of assay, but other assay formats can also be used. A monomeric reland will demonstrate no more than about 1%, and preferably less than about 0.2%, of the binding activity of analyte. Typically, in an ELISA test, binding activity is represented by titer, i.e., dilution or concentration of receptor with a particular binding activity. Alternatively, specific activity at the same receptor concentration can be compared.

The microtiter plate method of evaluating a reland takes advantage of the ability of multimer reland structures to exhibit increased association constant. When the microtiter plate is coated with a potential reland candidate conjugated to protein, the complementary labeled antibody is added and a complex allowed to form. If the reland is suitable, release of the labeled antibody from the complex will occur and can be detected in a sample supernatant after sample containing analyte is added. A microtiter plate format is used for screening for potential relands because of its ease. To quickly and easily screen potential relands, microtiter plates are pre-coated with albumin at a concentration of 2 ug/ml. The various reland candidates bearing —COOH or $—NH_2$ groups are added with carbodiimide to the wells and allowed to interact with the albumin overnight. After washing, the reland-coated plate can be tested, first to evaluate its ability to bind antibody, and then for its ability to release. In this format, it is possible to screen dozens of reland candidates quickly and simply in a day or so.

Release Assay Format

The release assay comprising receptor, reland and a means for detection of released reland or receptor (when it is desired to detect released receptor) provides a rapid, easy, and inexpensive method of detecting analytes.

Analytes may be those generally described previously herein. Specific embodiments are directed to theophylline, glycated hemoglobin, metabolic products of nicotine such as cotinine, and C- and N-terminal peptide markers of bone and collagen turnover such as telopeptides and pyridinolines especially suitable in monitoring osteoporosis.

The method of the present invention is a direct assay in that it yields a positive result in detecting the dissociation of a receptor:reland complex. That is, the presence of an analyte for the receptor results in the release of the labeled component as a positive event instead of no event or a negative event as in prior art assays. A positive correlation is advantageous because it is psychologically satisfying that presence of signal or increase in signal intensity indicates presence of analyte in a sample. Results obtained by assay methods in which detection of signal decreases when analyte is present are susceptible to misinterpretation. It is desirable to employ an assay, such as that of the present invention, in which only a positive result generates signal. Assays of the invention are equally suitable for use both in a laboratory by technical personnel as well as outside a laboratory by both technical and non-technical personnel.

In a heterogeneous release assay, preferably the reland is labeled so that upon release in the presence of analyte, the reland-label is separated from reaction products and the label detected. In a homogeneous release assay, while it is preferred that the reland be labeled, under certain circumstances the receptor can be labeled instead. For example, a fluorescent label may be used on the receptor, in which case the reland may contain a fluorescence quencher. In the receptor:reland complex, the fluorescent signal is thus quenched, and there is no fluorescence detectable until release of reland occurs in the presence of analyte. Suitable labels include enzymes, enzyme inhibitors, fluorophores, cofactors, chromophores, colloidal gold, dyes and chemiluminescent agents, and radioactive labels, all of which are well-known in the art. The specific means for detecting dissociation of a receptor:reland complex depends in part on whether the assay is homogeneous or heterogeneous.

Once suitable receptor, reland and detecting means are chosen, the assay system should be optimized for use with a particular sample matrix. A urine sample will have different intrinsic characteristics than a sample in aqueous buffer. The same is true for sample from saliva, blood, plasma or serum, or any body fluid. The assay may be optimized by varying reagent concentration, buffer composition, release time, detection time, baseline controls, and other variables. These variables are well-known in the art, and their adjustments for optimum assay specificity and sensitivity with a particular assay matrix will be readily understood by those skilled in the art.

Homogeneous Release Assays

The release assay may be performed in a homogeneous liquid phase. Such an assay is preferred because it can be performed in a single reaction vessel, and thus is well-suited for use in automated analyzers or on a membrane and, therefore, suitable for on-site testing.

A receptor:reland complex in a homogeneous release assay comprises a suitable label system as a detection means in which the label activity is preferably not appreciably detectable prior to the release of the reland. This lack of detectability is generally a consequence of the properties of the label and the complex which manifest themselves in the form of activity modulation such as attenuation, inhibition, or activation of the detection system. The intensity of the signal from the label is increased or decreased upon formation or dissociation of the complex. The labels may include for example, a fluorescent, a chemiluminescent or an enzyme label attached to the reland and an appropriate quencher attached to the receptor. The receptor may itself be a quencher. The signal will be quenched and no signal will be observed. However, upon dissociation of the receptor:reland complex and release of the receptor and reland in the presence of analyte, the effects of the modulation will be reversed and label will be appreciably detectable. Other proximity-dependent signal attenuators, such as fluorescence polarization, are known in the art, and can be adapted for use in a release assay. Alternatively, the reland can be labeled with a cofactor label, a dye-label, an enzyme inhibitor, or another type of label that is detected after release such as the FAD component of glucose oxidase described previously herein. It will further be appreciated that the label may be on the receptor and the quencher on the reland.

Heterogeneous Release Assays

In another embodiment, a heterogeneous solid/liquid phase release assay is provided. In such an assay, receptor is irreversibly absorbed to a solid phase support. As used herein, the term "irreversibly absorbed" includes covalent, non-covalent, and ionic association. Solid phase supports include plastic, polymer beads, glass beads, glass, silica gel, and plastic microtiter plate wells and membranes such as nylon and nitrocellulose membranes. However, the release assay is not limited to a particular choice of solid phase support and any solid phase support known in the art may be used.

The reland is labeled, and a stable complex comprising the labeled element and the receptor on the solid phase element is formed. Once a stable receptor:reland complex is formed, it can be exposed to sample. If the analyte of interest is present in the sample, the release reaction occurs and signal from the label is detected in the liquid phase. The extent of release, and thus the signal intensity in the liquid phase, positively correlates with the amount of analyte in the sample. The actual concentration can be obtained from standard curves obtained or prepared in accordance with techniques well-known to those skilled in the art. The signal intensity of the solid phase decreases inversely with the amount of analyte in the sample.

Many labels can be used in the heterogeneous release assay. Labels such as cofactors (e.g., FAD), inhibitors chromophores, fluorophores, chemiluminescent agents, radioisotopes, chelating complexes, dyes, colloidal gold, secondary labels (e.g., biotin or a hapten), and the like can be detected in the liquid phase after the release reaction as increased enzymatic activity, optical density, fluorescence, luminescence, radioactivity, color (for dyes), detection of the secondary label (e.g., using avidin or streptavidin to detect biotin, or a hapten specific antibody to detect the hapten), and turbidity (for colloidal gold), respectively. Where the signal from label that remains bound in the receptor:reland complex cannot be detected, the assay may be performed without a separation step, for example, in a single vessel.

In a particular embodiment preferred for non-laboratory settings, the presence of an analyte is indicated by the appearance of a shape, i.e., a letter, in a reaction field on a solid phase support. Accordingly, a reaction field comprising an indicator zone and a control zone is prepared on a solid phase support. The indicator zone comprises immobilized receptor as provided by the heterogeneous assay format. A receptor:reland complex in the indicator zone is sensitive to the release reaction. The control zone comprises a different receptor:ligand or reland complex or merely a different color. The receptor-ligand or reland complex in the control zone is not susceptible to the specific release reaction, but may indicate non-specific release if conditions are such as to cause non-specific release.

In practice, contacting sample containing the analyte of interest to the reaction field will result in a detectable release reaction in the indicator zone, and no reaction in the control zone. The release reaction is detected as formation of a contrasting zone corresponding to the indicator zone. To accomplish this, label for both the release complex and the control complex is chosen to contrast with the solid support.

If there is no development of a contrast zone, the sample is negative. "Fade" of both the indicator zone and control zone, i.e., release of label from both complexes, indicates a false positive reaction, inappropriate reaction conditions, or possible adulteration of the sample. In this way, the control zone provides a control for accurate assay results. In an alternative embodiment, the reaction zone on which a blue receptor:reland complex is immobilized, is yellow. Release of reland (blue color) which originally obscures the yellow color, causes a color change from blue (negative) to green (slight positive) to yellow (strongly positive).

Preferably different letters or symbols are used as the indicator depending on the analyte of interest. For example, indicator zone specific for cocaine use may be shaped like the letter "C"; an indicator zone for marijuana use shaped like the letter "M" (or "T" for tetrahydrocannabinol), and a zone to indicate nicotine use shaped like the letter "N".

It is clear that other receptor:reland combinations will work equally well as control complexes. It is further envisioned that a single solid phase support can contain more than one detection field, since each detection field is specific for a particular analyte and insensitive for any other analyte. Thus, the invention provides an assay for multiple analytes, e.g., tetrahydrocannabinol, benzoylecgonine, and cotinine, in a single format.

Suitable labels for use in this assay include but are not limited to colored dyes, colloidal gold, and the like. Also, any solid phase support can be used in this embodiment, but plastic and membranes, such as nitrocellulose or nylon, are preferred. In addition, the solid support, a membrane for example, can carry a series of labeled reland:receptor complex lines arranged in bar code format, each line/bar specific for a different analyte. When such member is dipped for example into a test ligand, such as milk, saliva, urine, blood, environmental sample or the like, the presence of an analyte specific for a bar will cause loss of the labeled reland from that bar causing a change which can be read by the bar code reader.

In another embodiment, FAD is conjugated to the reland. The strip is a membrane comprising a FAD-reland:receptor complex, apoglucose oxidase, glucose, horseradish peroxidase (HRP), and a chromogen tetramethyl benzidine (TMB). Considered together, the FAD, apoGO, glucose, and HRP constitute the means for detecting release. Contacting sample containing analyte with the membrane results in release of reland/FAD which is then free to activate with apoGO which oxidizes glucose producing $H_2O_2$ which is then reduced by the TMB to result in a blue colored oxidized form of TMB. This system may be manufactured in the same manner used to manufacture strips for measuring blood glucose.

In yet another embodiment, the receptor:reland/FAD complex is immobilized at the base or "bull" of a thermometer-shaped membrane. The strip above the base contains immobilized apoGO and peroxidase. Release of FAD/reland by analyte causes the FAD/reland to migrate along the length of the ApoGO-impregnated and bind to apoGO. The apoGO is now converted to the active enzyme which then starts the color-producing reaction referred to in the previous paragraph. That portion of the length of the strip or the height of the column which is activated in proportion to the amount of FAD/reland released changes color and can be read visually as a thermometer would be read. For example, a scale of numbers corresponding to concentrations can be provided along the length of the strip. Alternatively, instead of a numbered scale, the reading area can be divided into color zones indicating semi-quantitative readings. For example, specific colors could be assigned to low, medium, high, very high concentrations. In another preferred embodiment, the above "thermometer"-shaped strip is in a laminated device as described in Serex's U.S. patent application Ser. No. 08/047,156 filed Apr. 13, 1993, now U.S. Pat. No. 5,500,375, by Lee Own and Fitzpatrick.

The invention will be further illustrated by the following Examples, which are intended to be purely specific embodiments of the invention. Indeed, various modifications of the invention in addition to those shown and described herein become apparent to those skilled in the art from the description and accompanying drawings. Such modifications are intended to fall within the scope of the appended claims.

EXAMPLE 1

Release Assay for Cotinine

Cotinine and trans-3'-hydroxycotinine are the major metabolites of nicotine (Langone et al., 1973, Biochem. 12:5025–30; Jacob et al., 1991, J. Chromatography 222:61–70; Neurath et al., 1987, Int. Arch. Occup. Environ. Health 59:199–201). They appear in urine in a 1:3 ratio (Neurath et al., supra). The detection of cotinine in urine, serum or saliva is the most commonly used biochemical method to determine levels of exposure to nicotine (Fitzpatrick, 1991, Clinical Chemistry News, vol. 11). Unlike other drugs of abuse, cotinine is found in body fluids of non-users due to passive smoking. The range of interest for a cotinine assay is from 0.010 ug/ml necessary for saliva and blood testing, to 10 ug/ml for urine of tobacco users (Greenberg et al., 1984, N. Engl. J. Med. 310:1075–78; Matsukura et al., 1984, N. Engl. J. Med. 311:828–31; Sepkovic et al., 1985, Am. J. Public Health 75:663–6; Sepkovic et al., 1986, J.A.M.A. 256:863; Jarvis et al., 1987, Am. J. Public Health 77:1435–8; Schepers and Walk, 1988, Arch. Toxicol. 62:395–7; Langone et al., 1988, J.I.M. 114:73–8).

In this Example, cotinine release assays using N-propylcarboxylnorcotinine and N-isopropylcarboxylnorcotinine as very low affinity relands are described. Cis 3'-hydroxycotinine was also evaluated. The release assays were performed in a homogeneous format similar to the EMIT$^R$ assay and heterogeneous format (microtiter plate, ELISA format) and compared to a conventional competitive assay for cotinine. The results demonstrated that the release assays of the invention are more precise and exhibit less interference from cross-reactivity than known assays. Moreover, the release assay of the invention has a standard curve that is linear, r=0.999 (see FIG. 4), and a dynamic range that is almost 3 logs greater than currently known competitive, or dissociation or sandwich assays.

The following materials and methods sections set forth general descriptions of the reagents prepared and used in the assays, as well as the methods employed.

Materials and Methods

Instrumentation included an SLT Lab Instruments 340ATTC Microtiter Plate Reader, and COBAS MIRA Autoanalyzer. Urine samples were from a general population previously analyzed for cotinine. Samples were stored at −20 degrees C.

All chemicals were from Sigma Aldrich unless otherwise stated. Cis and trans-hydroxycotinine were purchased from the laboratory of George Neurath (See Neurath et al., supra).

Glucose-6-phosphate dehydrogenase (G6PD) was from Beckman. The Nicotine Metabolite Assay Kit, NiMA AutoMates$^R$, and the ELISA Kits, Tobacco Screen$^R$, and the Cotinine Trace Quantities CotiTraq$^R$tests, TMB chromogen system, anti-Cotinine antisera, peroxidase labelled anti-Cotinine, and Cotinine urine standards are commercially available from Serex, Inc. (Maywood, N.J.).

The Receptor

Antiserum to carboxylcotinine was obtained as follows: 320 mg of keyhole limpet hemocyanin (KLH) were dissolved in 40 ml of deionized water. To this were added 300 mg of trans-4-carboxylcotinine with mixing until dissolved. 300 mg of 1-ethyl-3-di-methylaminopropyl carbodiimide (EDC) were added to the reaction mixture with stirring and stirred overnight at room temperature. The KnH-carboxylcotinine conjugate (immunogen) was dialyzed for 8 hours at 2–8 degrees against phosphate buffered saline. The dialysis fluid was changed once after 4 hours.

Rabbits were immunized with the immunogen in Freund's adjuvant, with multiple injections over several months according to standard protocols. Test bleedings were made at defined intervals, and increases in antibody titer measured using an enzyme immunoassay for cotinine. Measurements of antibody affinity and cross-reactivity were also performed. When these assays indicated satisfactory antibody performance, rabbits were bled and sera were isolated and pooled. Antiserum was stored at –40 degrees C.

The IgG fraction was separated from serum by ammonium sulfate precipitation. An immunoaffinity chromatography column was prepared by coupling succinylated hydroxycotinine through its carboxyl group to aminosepharose 4B. The affinity purified antibody was labeled with horseradish peroxidase using the sodium metaperiodate method.

Preparation of Relands

Figure 1C:
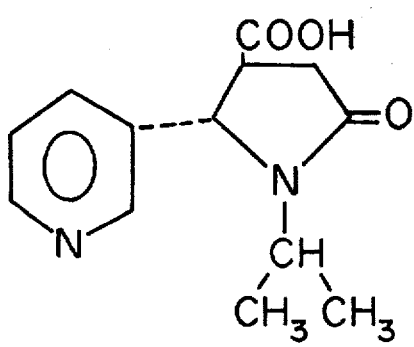
Figure 1D:
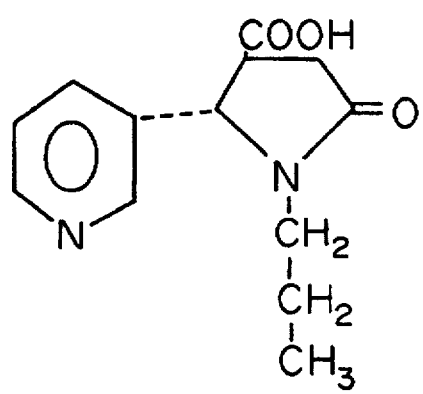

1-Isopropyl-4-carboxyl-5-(3-pyridyl)-2-pyrrolidinone, (hereafter, N-isopropylnorcotinine) and 1-propyl-4-carboxyl-5-(3-pyridyl)-2-pyrrolidinone (hereafter, N-propylnorcotinine) (FIGS. 1C and 1D) were prepared according to the method of Cushman & Castagnoli (1972, J. Org. Chem. 37:1268). Briefly, to a solution of 17 g of pyridine-3-carboxyl-aldehyde in 50 ml of benzene was added a benzene solution of 8 g isopropyl amine (or 8 g propyl amine) and 12 g molecular sieve pellets. The mixture was stirred at 20 degrees C. overnight in a flask. The solution was filtered through two layers of Whatman No. 2 filter paper and evaporated under reduced pressure to give the imine as a yellow oil. The structure of the products was confirmed by NMR.

N-isopropylnorcotinine and N-propylnorcotinine were prepared as follows. Twelve g of N-3-pyridylidene isopropyl imine or N-3 pyridylidene propyl imine and 15 g succinic anhydride were refluxed for 24 hours in 100 ml xylene. After the mixture cooled, the top layer was decanted and discarded. The residue brown oil was dissolved in 300 ml of 5% sodium bicarbonate solution, washed with two 250 ml portions of chloroform, and decolorized by absorption with 1 g activated charcoal. The suspension was filtered and the yellow filtrate heated on a steam bath to remove traces of chloroform. The pH was adjusted to 4.7 with phosphoric acid to precipitate the product. The crude carboxylic acid was collected by filtration and recrystallized from a boiling ethanol to give 4 g white crystal. The structure of each compound was confirmed by NMR.

Preparation of Glucose-6-Phosphate Dehydrogenase (G6PD) Conjugates

Conjugates of N-isopropylnorcotinine, N-propylnorcotinine and cis 3'-hydroxycotinine to glucose-6-phosphate dehydrogenase were prepared using the methods described by Rubenstein and Ullman (1975, U.S. Pat. No. 3,875,011). Briefly, to 1 ml of 0.1M sodium carbonate buffer, pH 9.0, were added 0.43 ml of glucose-6-phosphate dehydrogenase (2.8 mg), 20 mg of NADH (disodium salt), 10 mg of glucose-6-phosphate, and 300 ul of carbitol. The solution ("enzyme solution") was stored at 4 degrees C. to chill.

To an empty test tube were added 26 mg of N-propyl or N-isopropylnorcotinine, 12 mg of N-hydroxysuccinimide, 21 mg of dicyclohexyl-carbodiimide, and 1.0 ml of dimethylformamide. This mixture was left at room temperature for 1 hour to allow the activated cotinine ester to form. After 1 hour, 10 ul of the reaction mixture were added to the cold enzyme solution At 15 minute intervals until a total of 70 ul were added (90 minutes total). Fifteen minutes after the final addition of reaction mixture, the modified enzyme was dialyzed against five changes of 1 liter each of 0.055M Tris-HCl buffer, pH 7.9, for at least three hours each.

The G6PD is used as a label when conjugated to the reland and used in a homogeneous system. When the conjugated reland is used in a heterogeneous system, the G6PD is used not as a label, but as a carrier protein to enhance attachment of the hapten to the solid phase. When conjugated to G6PD, the reland is in multimer form and the association constant up to 5 logs greater than for the monomeric form. Reland in this form is not preferred if complexes with long-term, up to 6 months, stability are required as would be required if the complexes were to be supplied in a kit. For such purposes, reland under 5,000 Daltons is generally used.

Reagents for the Homogeneous Release Assay

Reagent solutions for the homogeneous release assay of cotinine were prepared as three separate solutions, reagents A, A+, and B. Reagent A consisted of glucose-6-phosphate dehydrogenase reland conjugate at a protein concentration of 0.74 ug/ml, 0.05M Tris buffer, 5 mM $MgCl_2$, 0.5 mM EDTA, 1.75 mg/ml glucose-6-phosphate, 0.5% BSA, and preservatives at pH 7.9. Reagent A+ consisted of antisera in reagent A buffer. Reagents A and A+ were mixed prior to use to form working solution A, which is stable for one week at 4 degrees C.

Reagent B consisted of NAD at 3.3 mg/ml in 0.02M Tris buffer, pH 7.0.

Cross-reactivity was tested with cotinine and/or trans-3'-hydroxycotinine solutions prepared as follows. To 10 ml of a negative urine pool were added 100 ug of cotinine or trans-3'-hydroxycotinine. The mixture was vortexed and serially diluted into the same negative urine standard to make solutions of 5, 2.5, 1.25, 0.62, 0.31 and 0.16 ug/ml of cotinine or trans-3'-hydroxcotinine.

To prepare the 1:3, cotinine:trans-3'-hydroxycotinine, solution, a 10 ml aliquot of negative urine standard was spiked with 100 ug of cotinine and 300 ug of trans-3'-hydroxycotinine. This solution was vortexed and serially diluted into the same negative urine standard to form dilutions of 5 (15), 2.5 (7.5), 1.25 (3.75), 0.62 (1.87), 0.31 (0.94), 0.16 (0.48) ug/ml of cotinine (hydroxycotinine).

Cross-reactivity was calculated using the following formula;

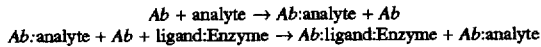

Release Assay in Elisa (Hetergeneous) Format

Corning microtiter plates were coated overnight with 100 ul of either glucose-6-phosphate dehydrogenase conjugated to N-propylnorcotinine or N-isopropylnorcotinine at 1 ug protein per ml of PBS; the wells were emptied, dried, and stored with desiccant until use. To activate for release, the plate was incubated 1 hour with 100 ul of horseradish peroxidase-labeled, affinity purified, anti-cotinine antibody. Excess antibody was removed by 2 washes with PBS in 0.05% Tween 20.

To a microtiter plate coated with a antibody:reland complex prepared above, 10 ul of urine standards (0, 0.5, 2, and 8 ug cotinine/ml) and 90 ul of distilled water were added to each well. After 2 minutes, 50 ul of the supernatant were transferred to uncoated wells containing 100 ul of TMB and incubated for 10 minutes. The reaction was stopped with 50 ul of 2N $H_2SO_4$ and read at $A_{450}$ nm.

Figure 2:
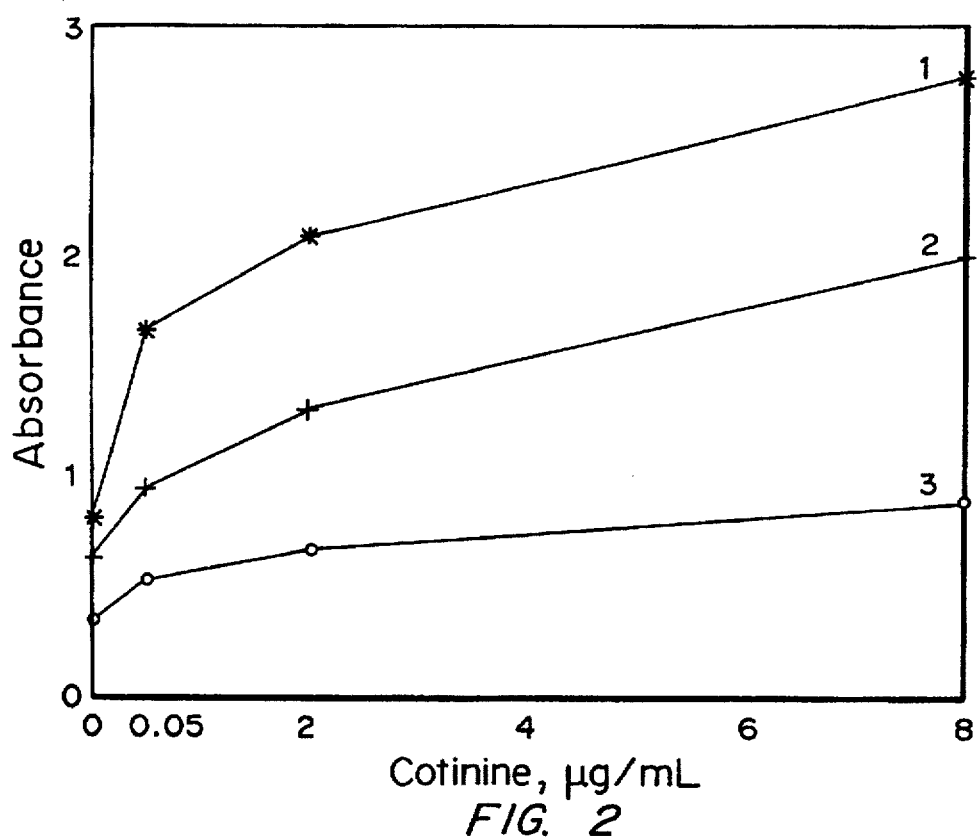
FIG. 2 ELISA format release assay for cotinine shows release from immobilized cis-hydroxycotinine G-6-PDH (asterisks); N-isopropyl-norcotinine G-6-PDH (plus signs); N-propyl-norcotinine G-6-PDH [open squares].

The results of the assay are shown in FIG. 2. Release of labeled antibody complexed to solid phase was detected in supernatant when free cotinine was present in the sample. Unlike conventional competitive immunoassays, absorbance or signal was directly proportional to analyte concentration. The best release characteristics were demonstrated by cis-hydroxy-cotinine (curve 1), followed the isopropyl cotinine (curve 2) with the N-propyl compound (curve 3) showing the least release. Despite the superior release from the hydroxycotinine conjugates, the hydroxcotinine compound is not considered to be a suitable reland in this system owing to its tendency to form a complex which over time becomes non-releasable. In the ELISA format the end-point release assay reduces the time for the assay to under 15 minutes (2 minutes for the release reaction and 10 minutes for TMB color development) from the 1–2 hours normally required in the conventional cotinine Elisa format. Time of the present assay could be further shortened, for example, by automating the assay steps such as by running a rate reaction assay on an automated instrument. The release assay also reduces the number of assay steps by at least half. A further advantage is that the release gives a positive signal in the presence of analyte.

The Conventional Homogeneous Assay.

The format of NiMA AutoMates[R] (trademark of Serex, Inc., Maywood, N.J.) is a homogeneous, competitive or EMIT-type assay, as described by Rubenstein, Schneider, and Ullman (1972, supra). There are two steps to the immune reaction:

Ab + analyte → Ab:analyte + Ab
Ab:analyte + Ab + ligand:Enzyme → Ab:ligand:Enzyme + Ab:analyte Briefly, sample was pre-incubated with antisera for several minutes. Into this reaction mixture was added glucose-6-phosphate dehydrogenase (enzyme) conjugated to cotinine ligand. Antibody that has not interacted with cotinine in the sample binds to cotinine on the glucose-6-phosphate dehydrogenase. The binding of antibody to the enzyme-linked ligand inhibits enzyme activity, thus the enzyme activity is directly related to the concentration of analyte in sample. Enzyme activity of glucose-6-phosphate dehydrogenase was measured by monitoring the formation of NADH at $A_{340}$ nm, which forms as the enzyme oxidizes glucose-6-phosphate to glucono-lactone-6-phosphate and reduces NAD to NADH.

The conventional homogeneous assays were performed on the COBAS MIRA according to the NiMA AutoMates[R] application sheet parameters as follows:

Two hundred ul of reagent A were incubated with 10 ul of sample at 37 degrees for 75 seconds. Fifty ul of reagent B were added and the mixture was incubated for 25 seconds. The absorbance was read over the final 250 seconds. Total time of the assay was 5.83 minutes.

The Release Assay In Homogeneous Format.

The homogeneous assay of the present invention, was performed on the Cobas Mira in the AutoMates[R] (trademark of Serex, Inc., Maywood, N.J.) format, utilizing the same enzyme system and the same reagents (except for the reland) as the conventional homogeneous assay, but modified as follows to become a release reaction.

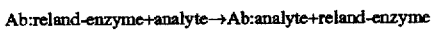

To make the Ab:reland-enzyme product, the reland:enzyme conjugate in buffer and antisera (Ab) in buffer were mixed for a minimum of one hour to form a working reagent A which is stable for 1 week at 4 degrees C. The reaction was started by addition of sample (25 ul) and NAD (10 ul-Reagent B) to two hundred ul of working reagent A (incubated for 25 seconds). The absorbance was read over the final 200 seconds. Total time of the assay was 5.0 minutes. As in the conventional competitive assay, enzyme activity was measured by monitoring the formation of NADH at $A_{340}$ nm. Enzyme activity is directly proportional to the concentration of analyte in the sample.

Figure 3:
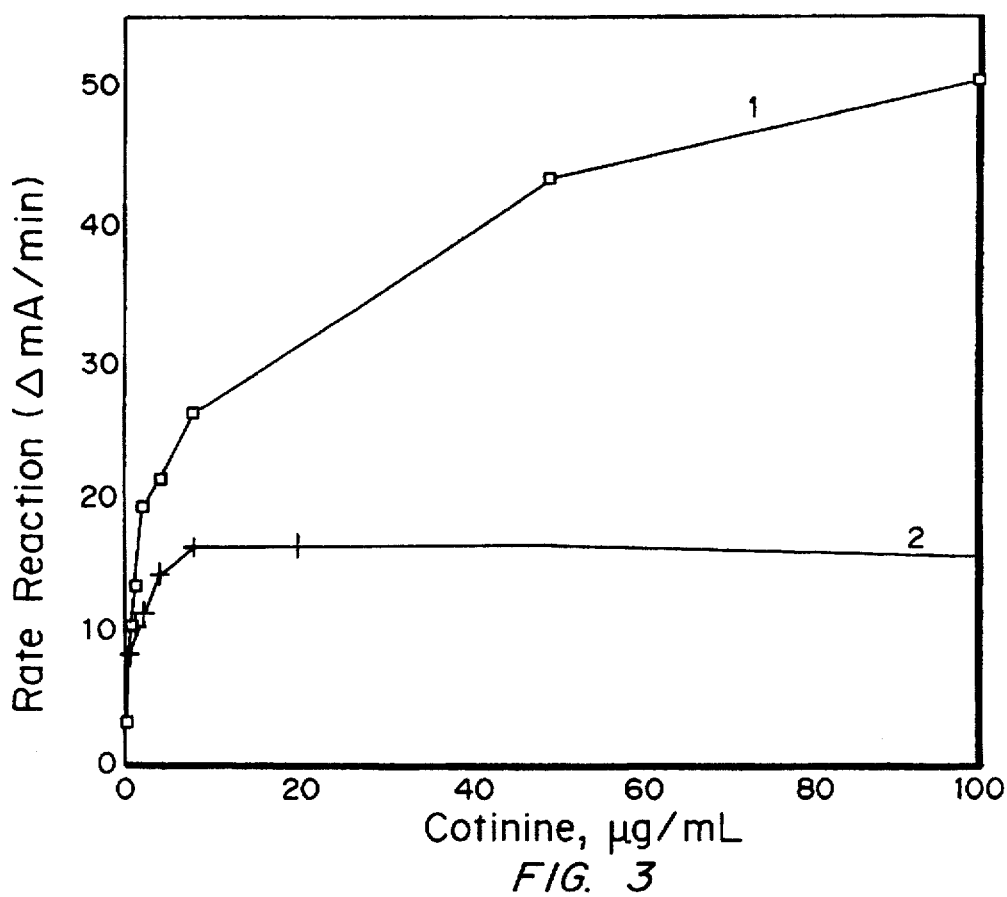
FIG. 3 Comparison of the dose response curves of a prior art homogeneous Emit assay type format (plus signs) for cotinine with a release assay of the invention for cotinine (squares).

Dose response curves for the conventional (NiMA[R]) (curve 2) and release homogeneous assays (curve 1) demonstrate the greatly increased range of the release assay (FIG. 3). As can be seen from FIG. 3, the maximum amount of cotinine that can be measured using the conventional competitive EMIT-type assay is 2 ug/ml. In contrast the release (curve 1) and FIG. 4 detects 1000 mg/ml. In addition, the lower end sensitivity of the release assay is 10 ng/ml as opposed to 50 ng/ml for the conventional assay (see Table 1). The range of the release assay is extended because the release assay is not competitive and because it is a system that starts in equilibrium. It is therefore possible to use higher starting concentrations of enzyme complex without increasing noise or losing low-end sensitivity. In conventional competitive immunoassays, addition of more reagents changes the sensitivity of the assay by shifting final equilibrium conditions. The enzyme concentrations used to demonstrate the release assay were 0.50 ug/ml as compared to 0.03 ug/ml for the conventional homogeneous (associative) assay. However, the conventional type assay had about 8 times more antibody per enzyme molecule than the release assay. The ratio of antibody to enzyme determines assay sensitivity.

Comparison of the competitive and release formats is presented in Table 1 below to show other variables.

TABLE 1

COMPARISON OF A HOMOGENEOUS RELEASE ASSAY FOR COTININE AND A CONVENTIONAL HOMOGENEOUS EMIT FOR COTININE (NiMA)

|  | RELEASE | NiMA-EMIT |
|---|---|---|
| Final Antisera Dilution | $4.8 \times 10^{-3}$ | $2.4 \times 10^{-3}$ |
| Final Conjugate Concentration | 0.51 ug/mL | 0.03 ug/mL |

TABLE 1-continued

COMPARISON OF A HOMOGENEOUS RELEASE ASSAY FOR COTININE AND A CONVENTIONAL HOMOGENEOUS EMIT FOR COTININE (NiMA)

|  | RELEASE | NiMA-EMIT |
|---|---|---|
| Antisera Dilution/ug Conjugate | $9.6 \times 10^{-3}$ | $80 \times 10^{-3}$ |
| Lower Limit of detection | 0.01 ug/mL | 0.05 ug/mL |
| Upper Limit of detection | 1000 ug/mL | 2 ug/mL |
| Time | 5 min | 5.8 min |

Figure 4:
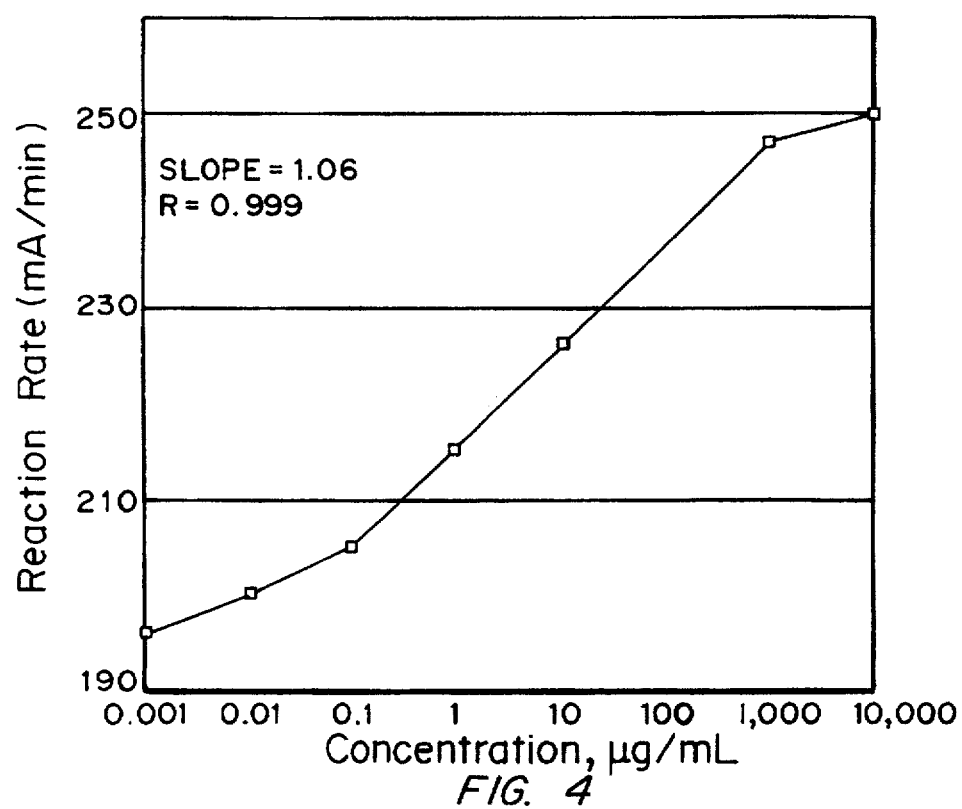
FIG. 4 Dose response curve of the release homogeneous assay of the present invention for cotinine.

Table 1 shows that the release assay utilizes 17-fold more enzyme and two-fold more antibody than the competitive assay. But the increased enzyme and antibody do not result in decreased sensitivity as they do in competitive immunoassays: (smaller amounts of all reactants could be utilized in the release assay, but this limits upper range of the assay). FIG. 4 shows the extraordinary range of the assay of from 0.01–1000 ug/ml. In the example shown, a 17-fold increase in reactants yields a greater than 1,000-fold increase in range of the assay, with no loss of sensitivity or precision at the low end of the curve. This formulation is sensitive to 10 ng/ml and can be used for quantitating saliva samples. The antibody to enzyme ratio of the conventional assay uses 8-fold more antibody per enzyme molecule than the release. In the release assay all antibody molecules can be bound to reland conjugated to enzymes and are capable of being released by analyte. In the conventional assay there is a large excess of antibody, which decreases reaction time, but also decreases sensitivity. The ability of the release assay to monitor the activity of a much larger percentage of the antibody in the reaction mixture increases sensitivity and decreases background noise and reaction time. Release here is from the multimer and is up to 100% indicating the inability of the multimer to substantially compete.

Cross-Reactivity: Trans-Hydroxycotinine

The greater specificity of the release assay relative to the conventional assay was confirmed by demonstrating (Table 2) that trans-3'-hydroxycotinine, a metabolite of nicotine, interferes (cross-reacts) far less in the release assay than in a conventional competitive assay. This is important because trans-3'-hydroxycotinine and other metabolites interfere in the detection system for cotinine in immunoassays.

TABLE 2

INTERFERENCE OF TRANS-HYDROXYCOTININE IN RELEASE AND COMPETITIVE (NiMA) HOMOGENEOUS ASSAYS FOR COTININE

RELEASE EMIT-TYPE HOMOGENEOUS ASSAY

| | COTININE SPIKE IN URINE | | TRANS-HYDROXY-COTININE SPIKE | |
|---|---|---|---|---|
| SPIKE CONC. (ug/mL) | CONCEN-TRATION FOUND (ug/mL) | % RECOVERY | CONCEN-TRATION FOUND (ug/mL) | % RECOVERY |
| 10 | 9.03 | 90 | 1.69 | 16.9 |
| 5 | 4.22 | 84 | 0.72 | 14.4 |
| 2.5 | 2.15 | 86 | 0.29 | 11.6 |
| 1.25 | 1.15 | 92 | 0 | 0 |
| 0.62 | 0.63 | 102 | 0 | 0 |

TABLE 2-continued

INTERFERENCE OF TRANS-HYDROXYCOTININE IN RELEASE AND COMPETITIVE (NiMA) HOMOGENEOUS ASSAYS FOR COTININE

| 0.31 | 0.25 | 81 | 0 | 0 |
|---|---|---|---|---|
| 0.16 | 0.14 | 88 | 0 | 0 |
| AVG |  | 89 |  | 6.1 |

CONVENTIONAL EMIT[R]

| | COTININE SPIKE | | TRANS-HYDROXY-COTININE SPIKE | |
|---|---|---|---|---|
| SPIKE | CONC. FOUND (ug/mL) | % RECOVERY | CONCEN-TRATION FOUND (ug/mL) | % RECOVERY |
| 10 | 11.85 | 119 | 1.87 | 18.7 |
| 5 | 5.6 | 112 | 0.85 | 17 |
| 2.5 | 2.03 | 81 | 0.44 | 17.6 |
| 1.25 | 1.59 | 127 | 0.21 | 16.8 |
| 0.62 | 0.59 | 95 | 0.17 | 27.4 |
| 0.31 | 0.49 | 158 | 0.11 | 35.5 |
| 0.16 | 0.13 | 81 | 0.08 | 37.5 |
| AVG |  | 110 |  | 24.4 |

While the release assay showed one-fourth the cross-reactivity with hydroxycotinine of the conventional assay, there was no cross-reactivity at the low end of the curve, i.e. where the concentration in clinical practices are critical. Significantly, the greatest amount of interference in the conventional assay was seen at the low end of the curve, i.e. the very portion of the assay in which no cross-reactivity is desired.

Cross-Reactivity of N-Isopropyl Norcotinine

To further test the stability and releasability of the antibody-reland complex we characterized the ability of N-isopropylnorcotinine to interfere in the various Serex cotinine assays, all of which used the same antibody. Results are shown in Table 3.

TABLE 3

CROSS REACTIVITY FOR N-ISOPROPYL-4-CARBOXYL-NORCOTININE IN CONVENTIONAL AND RELEASE ASSAYS

| | % CROSS REACTIVITY | | | |
|---|---|---|---|---|
| RELAND-SPIKED URINE (ug/mL) | HETER-GENEOUS CONVEN-TIONAL CotTraq[R] Elisa | HOMO-GENEOUS RELEASE Emit | HOMO-GENEOUS CONVEN-TIONAL Emit NiMa |
| 0.24 |  | 0% | <0 |
| 0.5 | 0% | 0% | <0 |
| 2 | 0% | 0% | <0 |
| 4 | 0% | 0% | 0.05% |
| 10 | 0.3% | 0% | 0.11% |
| 100 | 0.3% | 0.4% | 0.24% |

The reland, N-isopropylcotinine, showed less than 0.4% cross-reactivity with the detecting antibody (same for all assays) even in concentrations as high as 100 ug/ml, a point well outside the physiological range. The reland shows no cross-reactivity with the antibody complexed to it on G-6-P-DH until 100 ug/ml.

Clinical Data

The release assay correctly identified the 106 clinical samples as smokers (greater than 0.5 ug/ml cotinine) and 34 as non-smokers (less than 0.5 mg/ml cotinine). The release homogeneous assay, NiMA AutoMates[R] and Tobacco Screen[R] (an Elisa test marketed by Serex for assays in urine samples for cotinine) were compared using a cutoff of 0.5 ug/ml cotinine. Table 5 shows that the release homogeneous assay of the invention correlates 100% with both test methods (Tobacco Screen[R] correlates 100% with HPLC results).

TABLE 4

COMPARISON OF RELEASE HOMOGENEOUS COTININE ASSAYS WITH THE CONVENTIONAL ASSAYS, TOBACCO SCREEN[R] (ELISA) AND NiMA (HOMOGENEOUS)

| TOBACCO SCREEN[R] | | | | NiMA[R] | | |
|---|---|---|---|---|---|---|
| | | + | − | | + | − |
| RELEASE | + | 106 | 0 | RELEASE + | 106 | 0 |
| | − | 0 | 34 | − | 0 | 34 |
| | | n = 140 | | | n = 140 | |

Assay Precision

The release and NiMA[R] homogeneous assays for cotinine were evaluated for precision on a COBAS MIRA using a negative, 0.5 ug/ml and 2 ug/ml urine samples (Table 6). Precision is used to indicate the coefficient of variation of repetitive tests on the same sample. The release assay showed a more than a two-fold improvement in precision over the competitive assay. Even though reactant concentrations are 17-fold higher than NiMA[R], the release assay had better precision.

TABLE 5

PRECISION OF THE RELEASE AND THE CONVENTIONAL NiMA HOMOGENEOUS ASSAYS FOR COTININE. RESULTS STATED ARE REACTION RATE IN mA/MIN.

| Negative Control 0.0 ug/mL | Cutoff Control 0.5 ug/mL | Positive Control 2.0 ug/mL |
|---|---|---|
| RELEASE EMIT[R] | | |
| n = 15 | n = 15 | n = 15 |
| avg = 177.79 | avg = 185.4 | avg = 194.56 |
| SD = 0.88 | SD = 0.89 | SD = 0.81 |
| CV = 0.5% | CV = 0.5% | CV = 0.4% |
| CONVENTIONAL EMIT[R] (NiMA) | | |
| n = 15 | n = 15 | n = 15 |
| avg = 49.52 | avg = 55.86 | avg = 58.27 |
| SD = 0.69 | SD = 0.75 | SD = 0.78 |
| CV = 1.3% | CV = 1.3% | CV = 1.3% |

The greater than two-fold improvement in precision seen with the release assay of the invention is probably multifactorial: the starting system is in equilibrium; only one reaction, dissociation, occurs; and the matrix, as evidenced by lowered cross-reactivity, probably has less effect on the reaction.

EXAMPLE 2

Release Assay for Osteoporosis Marker

The marker for an osteoporosis assay shown below is free pyridinoline, a well-known degradation product of bone and cartilage. The marker can be prepared according to the method of Akiba K. and Nakamura N., 1977, B.B.R.C, 76:1124.

Candidates for relands were chosen from pyridine analogs selected from the Aldrich catalogue. Two analogs, pyridoxamine and pyridoxal were labelled with biotin as follows:

Synthesis of Pyrodoxal-Biotin Conjugate

To a mixture of pyridoxal hydrogen chloride salt (5.7 mg, 0.028mmol) and biotin hydrazide (7.9 mg, 0.031 mmol) in DMF (1 mL) was added triethylamine (4.7 uL, 0.033 mmol). The mixture was stirred at 4 degrees C. overnight and the solvent was removed under reduced pressure. The residue was treated with 0.1% trifluoroacetic acid in $H_2O$ and the solvent was removed under reduced pressure. The residue was then recrystallized from methanol to give 5.0 mg of pyridoxal-biotin conjugate as an off-white powder.

Synthesis of Pyridoxamine-Biotin Conjugate

To a suspension of pyridoxamine hydrochloride (11.8 mg, 0.049 mmol) in 1.5 mL DMF was added triethylamine ($Et_3N$) (20.5 uL, 0.15 mmol). N-hydroxy-succinamidebiotin (18 mg, 0.054 mmol) was then added to the above clear solution and the resulting solution was stirred at room temperature for two hours. The reaction mixture was concentrated and the residue was purified by preparation TLC (1% $Et_3N$-10% MeOH in $CH_2Cl_2$) to give 10.1 mg of pyridoxamine-biotin conjugate as a pinkish powder.

Binding of Biotinylated Analogs to Antipyridinoline Monoclonal Antibody

Figure 12:
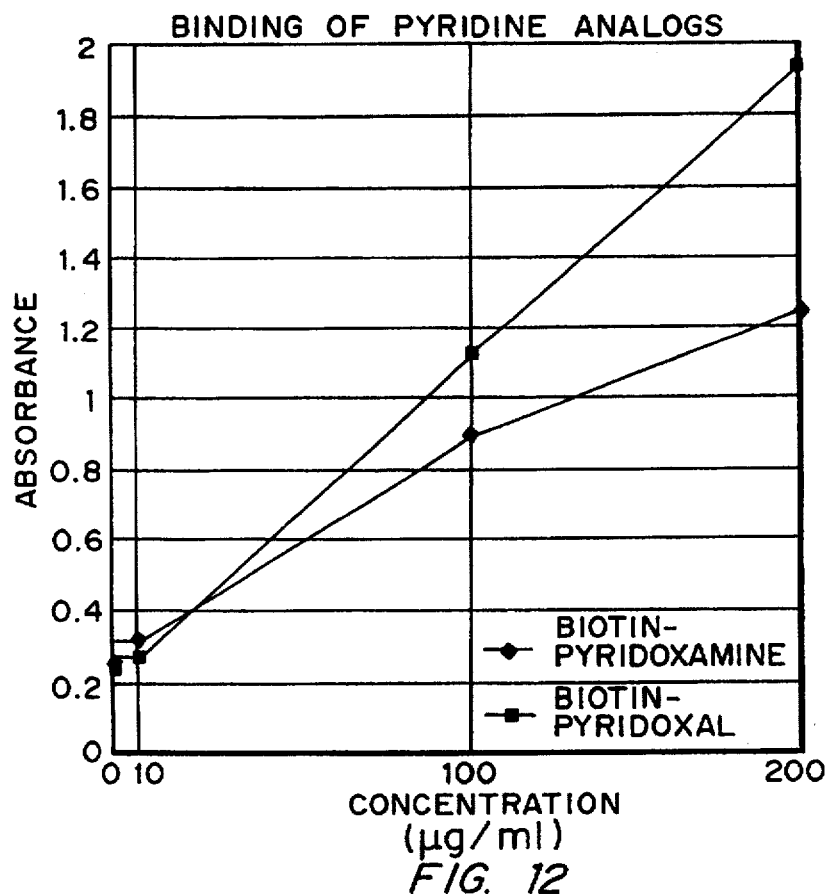
FIG. 12 Evaluation of the ability of pyridinoline reland candidates (i.e. Pyridine Analogues) to bind anti-pyridinoline in Elisa format.

Biotinylated pyridoxamine and biotinylated pyridoxal were bound to antipyridinoline antibody as follows:

Antipyridinoline (monoclonal antibody from the PYRALINKS KIT produced by Metra, Inc. of California) was coated on microtiter plate at a concentration of 4.6 ug/ml of PBS overnight at RT. Antibody coated plate was incubated with different concentrations of biotinylated reland candidate (10 ul of reland +90 ul of PBS 0.6% Tween 20, pH 7.4) overnight at 4 degrees C. The plate was then washed out and incubated 30 minutes with avidin-horseradish peroxidase conjugate (Jackson Immuno Research Lab., PA) at 0.1 ug/ml in a solution of bovine serum albumin, 1 mg/ml of PBS, pH 7.4, 0.06% Tween 20. After washing, bound peroxidase was measured with TMB. Amount of bound peroxidase was directly proportional to amount of biotinylated analog bound to antibody solid phase. Pyridoxal-biotin results are shown on FIG. 12. As can be seen, the biotin-pyridoxal conjugate resulted in higher binding to antibody.

Figure 13:
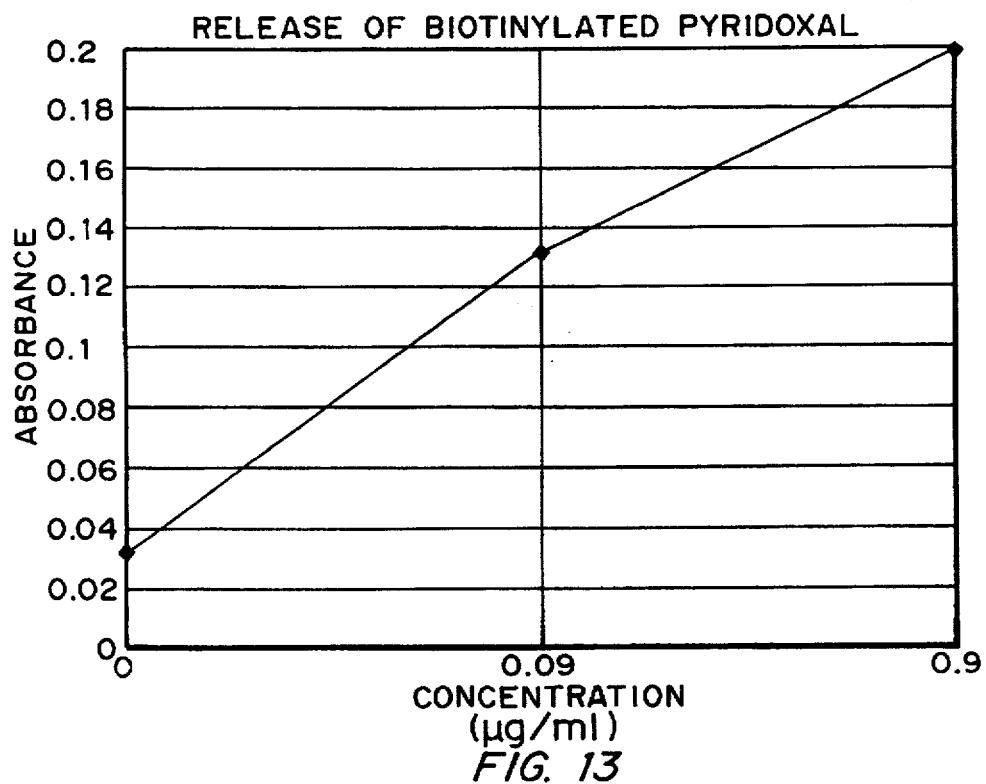
FIG. 13 Elisa format. release of biotinolated pyridoxal (Pyridinoline Reland) from anti-pyridinoline by Pyridinoline.

Release of Biotinylated Pyridoxal from Complex with Antibody by Free Pyridinoline Antipyridinoline antibody was coated on microtiter plate as described above. The antibody coated plate was incubated with 100 ul of biotinylated pyridoxal solution at final concentration of 200 ug/ml in PBS, pH 7.4 for 2 hours at room temperature. After washing, the plate was incubated with avidin-peroxidase Conjugate (from Jackson Imm. Res. Lab.) at 0.1 ug/ml in 1 mg/ml of bovine serum albumin in wash buffer, pH 7.4, for 30 minutes at room temperature. After washing off an excess of avidin-peroxidase conjugate, release with free pyridinoline (METRAsupra) was performed. 100 ul of different levels of pyridinoline (0, 0.09 ug/ml, 0.9 ug/ml) in PBS were added to the plate for 10 minutes at room temperature. Then 75 ul of the liquid phase was transferred to another microtiter plate and added to 75 ul of Serex TMB solution diluted 1/10 in deionized water. The amount of released peroxidase reflected the amount of biotinylated reland released from complex with antibody. Results are shown on FIG. 13.

EXAMPLE 3

Release Assay for Glycated Hemoglobin

This Example demonstrates the feasibility of a release assay for a protein, glycated hemoglobin (Hb Glc). Such a format will bring increased ease of performance and increased precision compared to conventional competitive or sandwich assays. In particular, the Hb Glc assay of the invention appears to have significant superiority over conventional assays in its ability to discriminate between glycated and non-glycated forms of hemoglobin (Hb).

Hb Glc constitutes up to 4% of the hemoglobin in a normal sample. This level can be 2-3 times higher in diabetics. Thus, Hb Glc is a useful prognostic indication of glycemic control over the previous month. There are three in vivo sites of glycation of hemoglobin at any one or more of the free epsilon amino groups, in addition to the glycation modification characteristic of hemoglobin A1C (Hb A1c). Hemoglobin A1c is hemoglobin that is glycated at the amino terminal valine of the beta chain of hemoglobin. The other three glycation sites on the molecule, may or may not be glycated in Hb A1c. In normal samples, 2-4% of hemoglobin may be Hb A1c, and this level can also be two to three times greater in diabetics.

Figure 5:
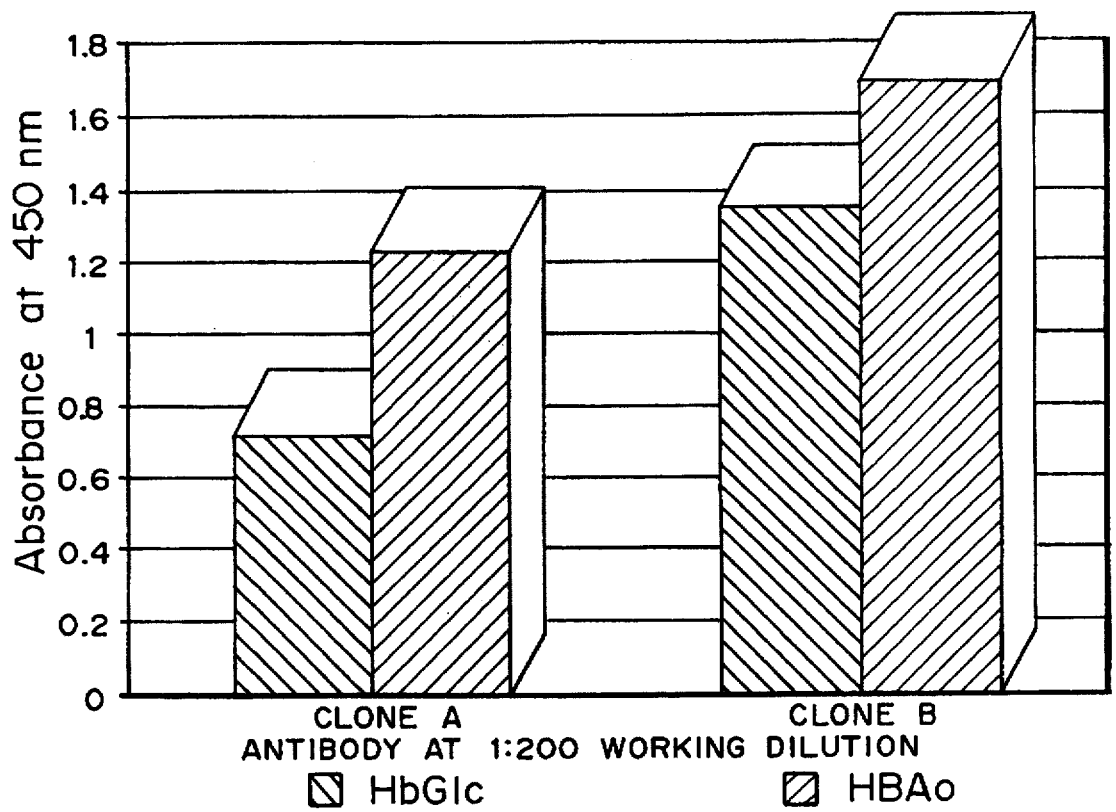
FIG. 5 Monoclonal antibody to glycated hemoglobin binds to nonglycated hemoglobin and glycated hemoglobin (HbGlc) in a conventional Elisa assay.

Two monoclonal antibodies specific for human glycohemoglobin were obtained from Exocell (Philadelphia, Pa.) Clone A 1.58 mg/ml E85.1A lot 94H 4.142, Clone B 2 mg/ml E85-1B lot 94C 3.01). HbAo (nonglycated Hb ) and Hb Glc were obtained from Exocell. The antibodies were each titered against glycated and non-glycated Hb both from Exocell as follows:

Conventional Assay Used for Evaluation. Microtiter Plate was coated with Hb Ao or HbGlc in PBS at a concentration of 10 ug/ml. Clone A and Clone B were diluted 1:20 in PBS and 100 ul was added to each well and incubated for 1 hour. The plate was washed with PBS and interacted with alkaline phosphatase labelled anti-mouse (Sigma A3688) for one hour. After washing, Alkaline phosphatase was detected with p-nitro-phenyl phosphate (PNPP) (Kirkegaard & Perry Labs, Maryland) for 60 minutes, FIG. 5. Both clones interacted with both glycated, darker pattern and non-glycated Hb. Clone B appeared to be more reactive.

The reactivity towards non-glycated Hb was between 50% and of that seen with glycated Hb. Thus, this antibody, in a conventional assay format where there is 90–98% nonglycated Hb+2–10% glycated Hb, is not highly specific for glycated hemoglobin.

The cross-reactivity between glycated and non-glycated hemoglobin seen with the Exocell monoclonal antibody was expected. There is only one small difference between nonglycated Hb and Hb Glc, which is the glycated lysine, with the remainder of the epitope the same in each molecule.

The sequence of hemoglobin to which both the antibodies are directed has been identified as the beta 17 (lysine) site, but it would appear that there is cross reactivity with the beta 66 site, which is very similar (both sites share a gly-lys-val sequence). In addition, the antibody is reported to react with both in vivo and in vitro glycated Hb. The sequences of the putative glycation sites are shown below:

| | |
|---|---|
| Beta Lys-17 | W G K V N V D |
| Beta Lys-66 | K A H G K V L G A |

A peptide having the sequence, acetylated-amino (Ac-) Trp Gly Lys Val Leu Gly Ala Gly Gly was prepared as a potential reland. This peptide, a hybrid constructed from both the above sequences was used at concentrations of 0.5 mg/ml in PBS pH 7.4 at room temperature in a treatment for six days with 0.5% glucose to achieve glycation. The glycated peptide was conjugated to albumin and used as solid phase reagent in an ELISA assay as follows:

Microtiter plates were coated with albumin at 5 ug/ml at pH 7.4 in PBS buffer overnight. The plate was then treated with carbodiimide (Sigma E6383) at a concentration of 10 ug/ml, and 100 ul of glycated peptide at 10 ug/ml was added and allowed to react overnight. Both clone A and clone B bound to the peptide, and neither was inhibited from binding by glycated hemoglobin. This demonstrated that the glycated peptide bound the antibodies too well and therefore did not qualify as a reland.

Since glycation of peptide together with conjugation created a product with too high an affinity for the antibody, the non-glycated peptide was selected as the reland. The reland was labeled for evaluation purposes by conjugation to biotin to form a reland-biotin conjugate. The product was purified by TLC and tested for ability to bind the anti-Hb Glc monoclonal antibodies.

In particular, the ability of the reland-biotin conjugate to be released by Hb and Hb Glc was tested. An antibody:reland complex was formed using Clone B, as Clone B had higher titer. Reland-biotin was separately incubated with each monoclonal Anti-Hb Glc antibody. After incubation for 72 hours at 4 degrees C, non-complexed reland-biotin conjugate was removed by ultrafiltration using Amicon CENTRICON-30 with membrane cutoff of 30,000.

Figure 6:
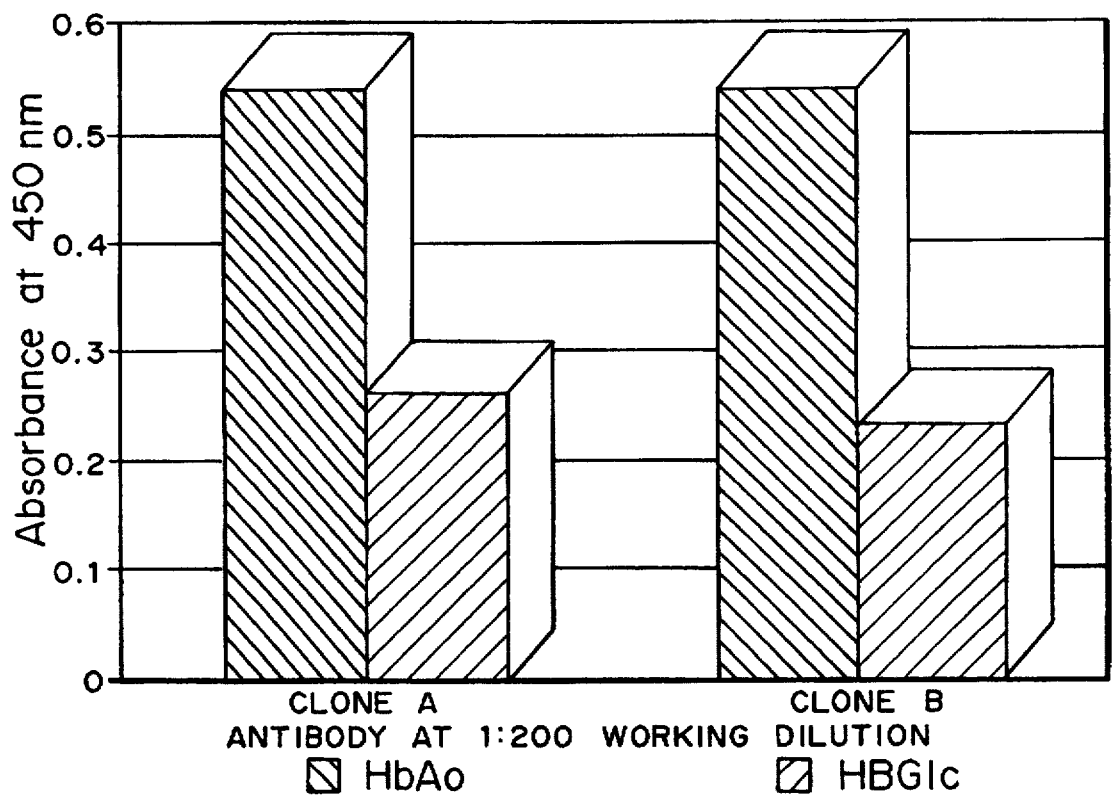
FIG. 6 Comparison of the ability of nonglycated hemoglobin (HbAo) and glycated hemoglobin (HbGlc) to release relands from monoclonal antibody to glycated hemoglobin.

Release of the reland by glycated Hb was tested: to the preformed antibody:reland complex were added either Hb Ao (Sigma) or Hb Glc, followed by incubation for thirty minutes. Hb Ao (Sigma) has been stripped of Hb A1C. Glycated Hb was prepared from Hb Ao (Sigma) by incubation with 0.5% glucose at PBS pH 7.4 for 7 days. The amount of release was measured as follows:

Following the incubation of complex with analyte, the entire mixture was transferred to an avidin-coated plate where all biotin label should bind, i.e., both released biotin-reland and non-released biotin-reland antibody complex. The amount of antibody bound to the plate detected with HRP-antibody was proportional to the amount of the non-released biotin-reland conjugate still complexed with the antibody. Therefore, a low absorbance is equal to a high degree of release. The data are shown in FIG. 6. These data clearly show greater release by Hb Glc than Hb Ao.

Figure 7:
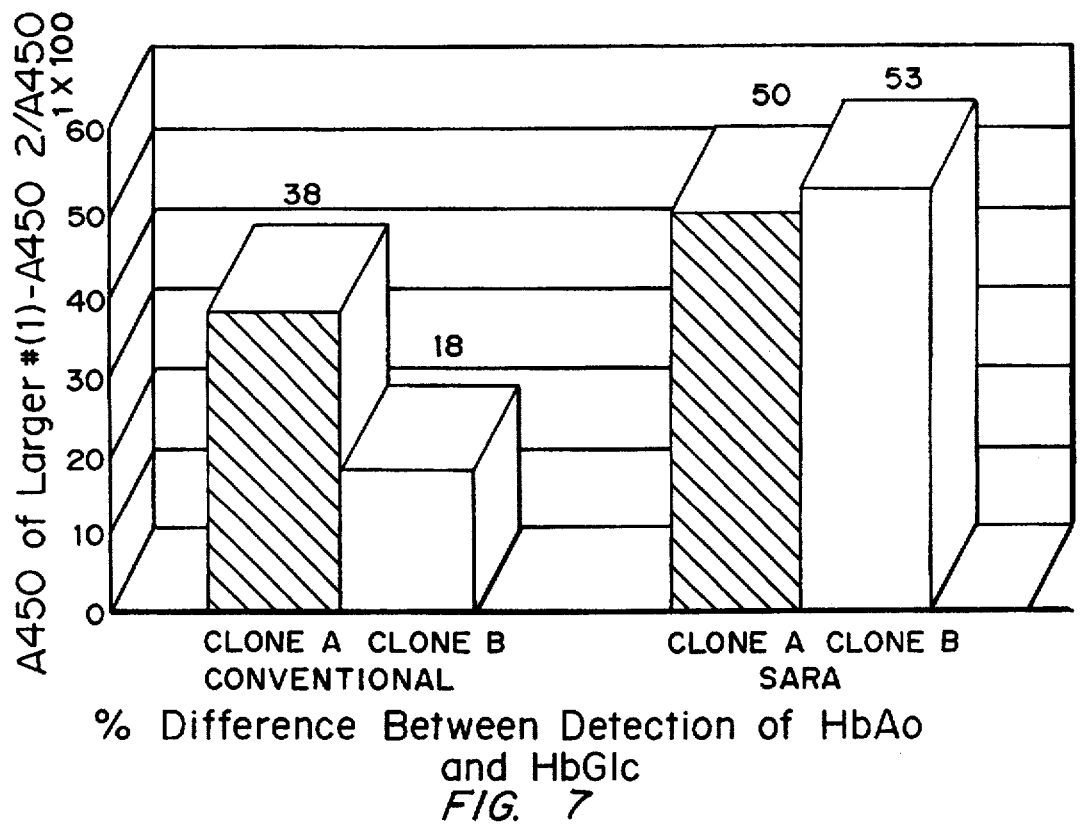
FIG. 7 Comparison of conventional with the Release Assay Format on the ability of monoclonal antibody to glycated hemoglobin to discriminate between glycated (HbGlc) and nonglycated hemoglobin (HbAo).

Glycated hemoglobin was able to release significant amount of the antibody bound to reland. This ability to discriminate between the non-glycated and glycated form significantly exceeded the ability of these clones to discriminate between the two forms in a conventional assay, as shown in FIG. 7.

EXAMPLE 4

Release Assay for Theophylline

This Example reports development of a release assay for theophylline. Theophylline is used in the treatment of asthma. It has a very narrow therapeutic range with too little being ineffective prophylactically and too much being highly toxic. Therefore, theophylline levels must be carefully monitored especially in children and in those taking other substances which might affect the metabolism of theophylline.

Figure 10:
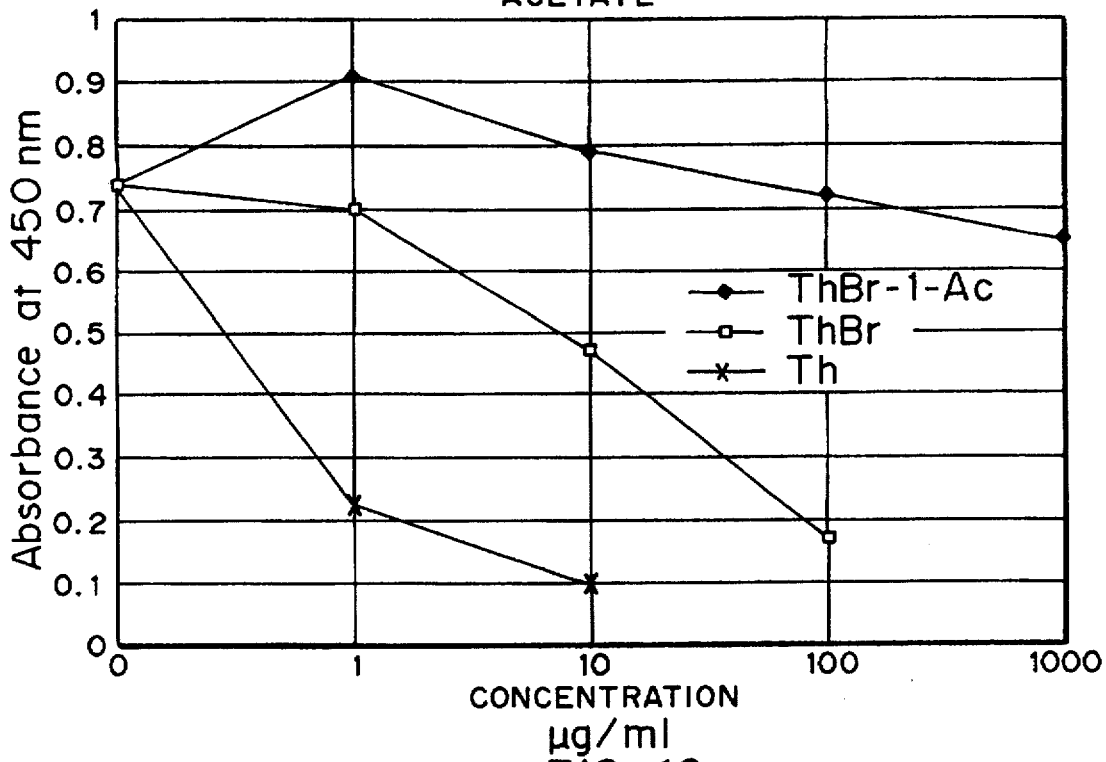
FIG. 10 Cross-reactivity of theobromine and theobromine-1-acetate in a competitive Elisa for theophylline.

Candidates for reland were selected by selecting compounds from the list of cross reactants provided by the antibody supplier. Theobromine with 0.6% reported cross reactivity was modified (see below) to allow for linkage to a label and evaluated for its cross reactivity in a competitive Elisa for theophylline as follows:

1-Acetyl-theobromine (ThBr-1-Ac) was compared with theobromine (ThBr) for the ability to compete with the analyte (in this case, biotinylated theophylline (Th)) for binding to antibody-coated plate in a conventional competitive-Elisa format (FIG. 10):

Anti-theophylline monoclonal antibody (theophylline 8) (OEM Concepts, Toms River, N.J.) was coated on microtiter plates at concentration 8 ug/mL. The antibody-coated microwells were contacted with theobromine and 1-Acetyl-theobromine at 0, 1, 10, 100, 1000 ug/mL and theophylline-peroxidase (from BiosPacific, Inc. Cat #V57520) at a dilution 1:500. The reaction was incubated for 1 hour at room temperature and after washing the amount of bound peroxidase activity was detected with Serex TMB diluted 1:20 in deionized water. As shown in FIG. 10, theobromine, but not theobromine-1-Acetate, was able to inhibit binding of theophylline to the antibody. Thus, theobromine-1-acetate could not significantly compete with the analyte for binding to the antibody, indicating its potential suitability as a reland in a release assay of the invention for theophylline. Also note that 20% increase in absorbance seen at reland concentrations of 1 and 10 ug/ml. This is a property commonly associated with relands.

Biotin conjugates of a competitive theophylline ligand, 8-carboxypropyldimethylxanthine; (8-CP-theophylline) and theophylline reland (Theobromine-1-Acetate) were synthesized as follows:

19 mg of 8 CP-theophylline (Sigma C4041) and 18 mg of ThBr-1-AC (synthesized according to Wolfes and Kornick German Patent No. 352980, 25 Apr. 1920) were converted to their active esters by N-Hydroxysuccinamide and dicyclohexylcarbodiimide (both from Sigma). Activated esters were interacted with 10 mg of 5-(biotinamido) pentylamine (Pierce, No. 21345) dissolved 0.6 ml distilled water at pH adjusted to 7 with sodium bicarbonate. Both biotin conjugates were purified by preparative thin-layer chromatography yielding homogeneous products.

Time-dependent complex formation of each of the biotin conjugates with the monoclonal anti-theophylline antibody (O.E.M. Concepts, Toms River, N.J.) was evaluated. To microtiter plates pre-coated with the anti-theophylline monoclonal antibody at 8 ug/mL in PBS pH 7.4, 10 uL of 40 ug/mL, 1 ug/mL and 0.25 ug/mL solutions of biotinylated ligand or reland and 90 uL of wash buffer (PBS+0.06% Tween 20) were added. The plates were incubated for 0, 5, 20, 60, 120, 240, 360, and 5400 minutes (90 hours), after which time the plates were washed. The amount of complex formation was determined by adding avidin-peroxidase (2.2 mg/mL diluted 1:80,000 in BSA-wash buffer) and incubating for 30 minutes. The avidin-peroxidase was removed, the plate washed with PBS, and the amount of peroxidase label was detected by adding 150 uL of TMB per well. The enzyme reaction was allowed to proceed for 15 minutes, followed by quenching with 50 uL of 2N $H_2SO_4$. The absorbance at 450 nm was measured.

The results are shown in FIGS. 8A, 8B, and 8C. FIG. 8A (binding of ligand and reland at 40 ug/ml) shows that binding of ligand-biotin conjugates was essentially complete after about 5 minutes. But reland binding required 360 minutes. At lower concentration, FIG. 8B (1 ug/ml) and FIG. 8C 0.25 mcg/ml, the binding of CP-theophylline was essentially complete after 5 minutes, but stable binding of theobromine-1-acetate reland required about a week of incubation. Note that time does not completely compensate for lower concentration.

Concentration Dependence of Reland Receptor Formation

Figure 11:
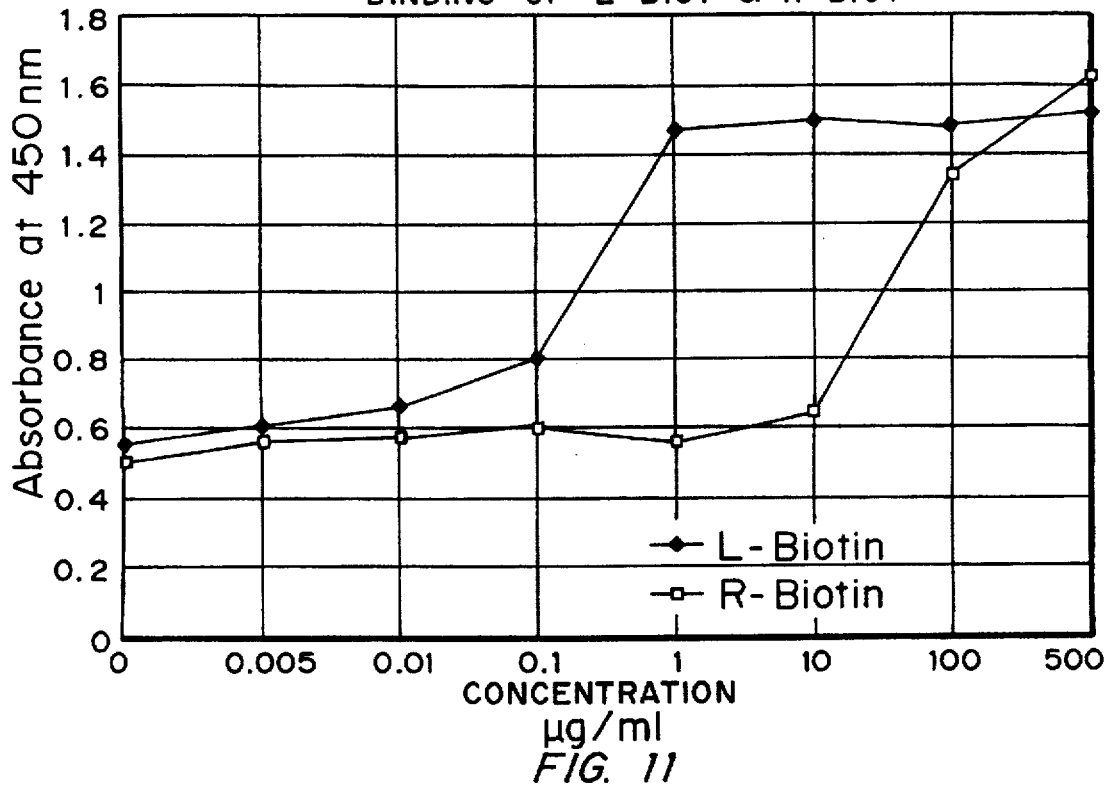
FIG. 11 Concentration dependence of theophylline reland (theobromine-1-acetate-biotin) receptor formation (squares) compared to that of theophylline ligand (carboxypropyldimethylxanthine) receptor formation (diamonds).

Microtiter plates were coated with anti-theophylline as described and incubated with biotin-reland (theobromine-1-acetate) and biotin:ligand, 8-CP Theophylline at concentrations of 0.005 ug/ml to 500 ug/ml (10 ul of biotin Conjugate+90 ul of PBS) for 1 hour at room temperature. Bound biotin was detected by incubation with avidin peroxidase (Jackson, Pa.) at 1:80,000 in PBS, 0.1% BSA 0.06% Tween. for 30 minutes at room temperature. Enzyme activity was measured using Serex TMB at 1:20 in dionized water for 15 minutes and stopping the reaction with 2N $H_2SO_4$. Results are shown in FIG. 11. Binding of ligand-biotin occurs at 1 ug/ml or $10^{-7}M$, while reland requires a >200 fold higher concentration of >250 ug/ml, i.e. $4.6 \times 10^{-4}$. We consistently observe that reland does not efficiently bind unless provided in a concentration in the range of $10^{-8}$ to $10^{-3}M$ most preferably between $0.5-5 \times 10^{-4}$.

Release Kinetics and Stability of the Complexes.

Figure 9A:
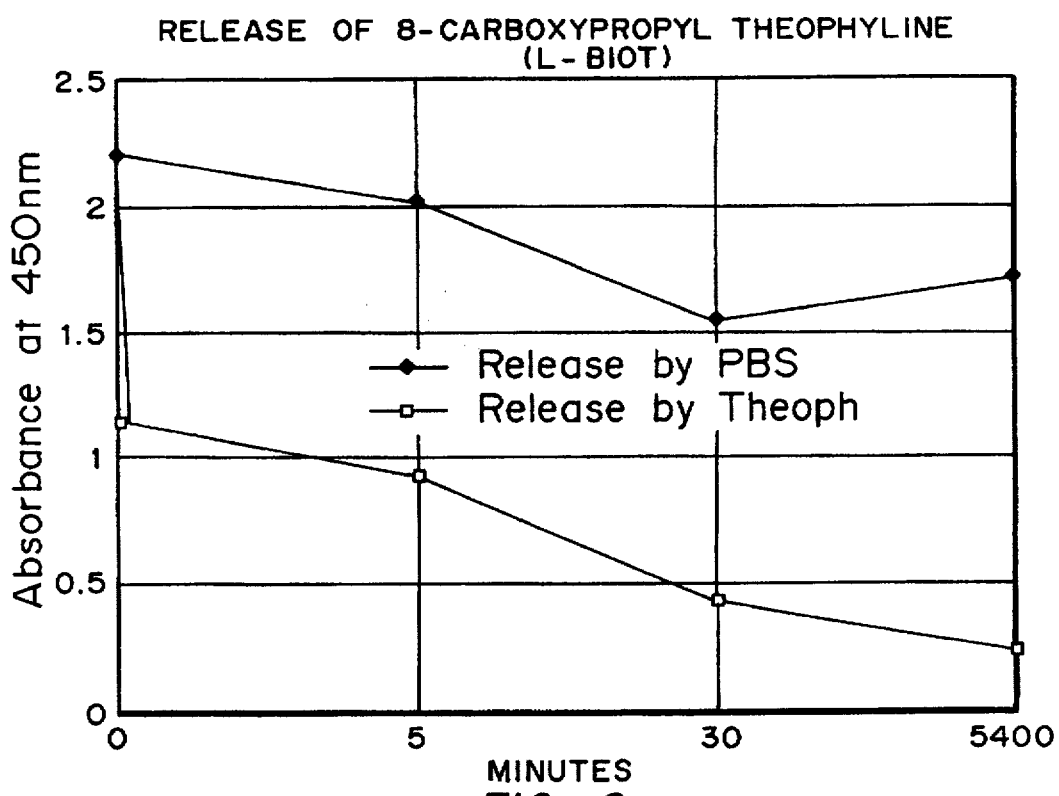
FIGS. 9A and 9B Release kinetics for ligand-biotin, carboxypropyldimethylxanthine-biotin, FIG. 9A, and reland-biotin, (theobromine-1-acetate-biotin), FIG. 9B. The amount of released biotin-ligand or biotin-reland was detected by detecting the ability of the released biotin to inhibit binding of biotin-horseradish peroxidase on a plate pre-coated with avidin.
Figure 9B:
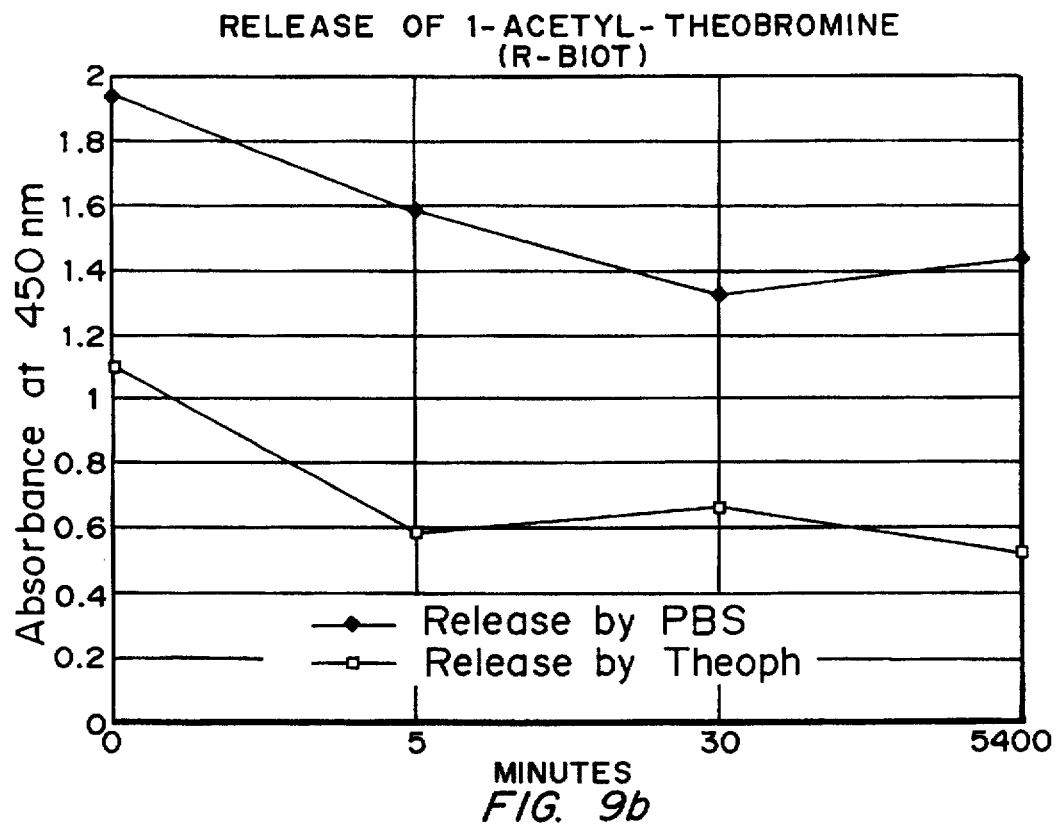

Release kinetics were evaluated for these biotin conjugates, FIGS. 9A and 9B. Release complexes were formed as follows:

To antibody coated (as above) on microtiter plates, 10 ul of each biotin conjugate at a concentration of 1 ug/ml for 8-CP-theophylline, ligand and 100 ug/ml for ThBr, reland, were incubated with 90 ul of PBS, 0.06% Tween 20, pH 7.4, on the plate for 1 hour at room temperature. After washing the plate, theophylline standard at 1 ug/ml or a PBS control was added. At the indicated times from 5 minutes to 90 hours, 75 ul samples were removed and assayed for release. The amount of released biotin-ligand or biotin-reland was detected by detecting the ability of the released biotin to inhibit binding of biotin-horseradish peroxidase (Jackson Immuno Research, PA) at 1:40,000 in PBS on a plate pre-coated with avidin (Sigma) coated at 10 ug/ml in PBS pH 7.4 overnight. The enzyme reaction was run for 15 minutes and was stopped with 2N $H_2SO_4$. Absorbance was read at 450nm.

The PBS control shows that for both ligand and reland there was loss of binding during the first thirty minutes but none during the remaining 90 hours. This thirty minute time during which there is spontaneous loss may represent the time during which the antibody:ligand or antibody:reland is assuming a more stable conformation with a lower dissociation rate than the initial immune complex. This indicates that the dissociation constant (Kd) of reland and ligand are similar and are both very low in contrast to Freytag who specifies a difference in the Kd.

When a complex of ligand, 8-CP-theophylline, was contacted with 1 ug/ml theophylline, significant release took 30 minutes, with further release throughout the 90 hours (FIG. 9A). In contrast, complete release of ThBr was almost instantaneous and required less than 5 minutes: and no further release occured confirming that for ThBr, the reland, release is independent of Kd.

EXAMPLE 5

Detection of Theophylline Using APO Glucose Oxidase in the Detection System for a Release Assay The theophylline reland used was theobromine-1-acetate, coupled to FAD as follows:

To 24 mg of theobromine-1-acetate dissolved in 1 ml of dimethyl formamide was added 13 mg of N-hydroxysuccinamide and 25 mg of dicyclohexyl carbodiimide. After 1 hour incubation at room temperature, activated theobromine-1-acetate was mixed with $N^6$ amino hexyl-FAD, synthesized according to the method of Carrico & Johnson (U.S. Pat. No. 4,255,566) in 0.1M carbonate buffer, pH9. Following overnight reaction, the crude preparation was purified by preparative TLC in a solvent system of ethanol/1M triethyl-ammonium bicarbonate (9:1). The final concentration of reland-FAD conjugate was determined spectrophotometrically using molar absorption coefficient of FAD at A450 nm. Anti-Theophlline (Biodesign, ME) having a cross-reactivity with theobromine-1-acetate-FAD of less than 0.01% was immobilized on Protein G agarose gel (1 mg Ab to 0.4 ml of Protein G agarose) by slow mix inverting on a rocker at 4 degrees C. overnight, followed by two washes by centrifugation.

Conditions for Reland Binding 30 ul of gel was distributed to wells of a Millipore Filtration device at the following concentrations. $3.35 \times 10^{-6}$M antibody/well $6.7 \times 10^{-6}$M binding sites) and was brought to a reland concentration of $2.9 \times 10^{-4}$M, $3.8 \cdot 10^{-5}$M, or $3.8 \times 10^{-6}$M. reland-FAD was allowed to bind for 2 hours at room temperature and then the gel was washed extensively followed by aspiration to remove unbound reland-FAD.

Detecting Reland/Fad Bound by Ab

A.

Antibody:reland-FAD complex was detected by adding 40 ul of 1 mg/ml ApoGO, incubating with shaking at room temperature for 15 minutes. ApoGO bound to the FAD of the complex. Unbound ApoGO was removed by aspiration. The amount of bound ApoGO was determined by addition to the wells of 20 ul horseradish peroxidase (2.5 ug/ml) and 50 ul of TMB/glucose (0.5 mg TMB/ml+500 mg gluc/ml). At two minutes the fluid was aspirated and absorbance at A620 nm was read in a SLT microtiter reader. 50 ul of 2N $H_2SO_4$ was added and absorbance at A450 nm was read:

| Molar Concentration of Reland:FAD | Absorbance at 450 nm |
|---|---|
| 0 | 0.09 |
| $3.8 \times 10^{-6}$ M | 0.09 |
| $3.8 \times 10^{-5}$ M | 0.15 |
| $2.9 \times 10^{-4}$ M | 0.83 |

At $2.9 \times 10^{-4}$ Molar concentration, significant binding occurs. Below $10^{-4}$, no significant binding occurs as was described in Example 4.

B.

To determine the dynamic range limits of the ApoGO detection system for FAD-reland, 60 ul of reland-FAD was added directly to the ApoGO detection solution and allowed to react for 3 minutes before stopping with acid as above, and absorbance at 450 nm was read:

| M Concentration of Reland:FAD | $^{A}450$ nm |
|---|---|
| $2.4 \times 10^{-6}$ | >2.0 |
| $2.4 \times 10^{-7}$ | 0.959 |
| $2.4 \times 10^{-8}$ | 0.204 |
| $2.4 \times 10^{-9}$ | 0.140 |
| 0 | 0.126 |

The background is very low. The detection range of the assay is $10^{-9}$–$10^{-6}$M within times that are useable for an on-site assay, i.e. under ten minutes.

C.

To evaluate release, immune complex was preformed as follows:

reland-FAD was interacted with anti-theophylline coated agarose as above using a reland concentration of $1.9 \times 10^{-4}$M and an antibody concentration of $5.15 \times 10^{-6}$. Excess reland-FAD was removed by centrifugation and with extensive washes. The immune complex-coated agarose beads were distributed into 8 wells of the filtration plate described above and aspirated. The release assay was performed by adding to the beads 60 ul of theophylline standard (theophylline Sigma T-1633) in PBS pH 7.4 and incubated 10 minutes with shaking. Released reland was aspirated, and then measured for its ability to activate ApoGO as follows:

To 60 ul of aspirant was added 30 ul of ApoGO at 1.5 mg/ml 25 ul of horseradish peroxidase at 2.5 ug/ml and 50 ul of TMB/Glucose (0.5 mg TMB per ml+500 mg glucose per dl). The reaction was stopped in 3 minutes with 50 ul of 2N $H_2SO_4$ and absorbance was read at A450 nm.

Release Results

| Concentration of theophylline | $^{A}450$ nm |
|---|---|
| 10 ug/ml ($5.4 \times 10^{-5}$M) | 1.571 |
| 1 ug/ml ($5.4 \times 10^{-6}$M) | 1.425 |
| .5 ug/ml ($2.7 \times 10^{-6}$M) | 1.324 |
| 0 | 0.548 |

Note that complete release is seen at 0.5 ug/ml. Sensitivity of the test is between $10^{-7}$ and $10^{-6}$M and that maximum release is achieved at about $10^{-6}$M indicating that at $2.7 \times 10^{-6}$M all FAD-reland has been released. It is estimated that 30 ul of coated beads in the reaction mixture has a maximum of $5.5 \times 10^{-6}$M of Ab so that maximum reland capacity would be about $10 \times 10^{-6}$ further indicating that release was complete, i.e. that reland was 100% released. The above complex could be stored for several days with no change in reactivity.

The same reagent system was used on a Pall Biodyne B nylon membrane and read visually to yield similar results. In the membrane format, the immune complex is separated from the ApoGO by physical separation on the membrane either on the same surface, or by placing some reagents on the opposing surface. For example, we have demonstrated that Pall biomembranes can be impregnated on either side without penetration to the other side, thus providing physical separation or through the use of a second membrane in contact with the first. As FAD-reland is released by analyte, it migrates to the ApoGO and other detection reagents and generates a color directly proportional to the released reland/FAD and the concentration of analyte.

Discussion

Heterogeneous Format

While assay systems that involve dissociation of preformed antibody-ligand complexes (Cocola et al., 1979, Analytical Biochem. 99:121–8-Hinds et al., 1984, Chin. Chem. 30:1174–8; Hinds et al., 1985, Chin.Chem.Acta 149:105–15) have utilized competitive ligands as binding partners, release assay of the invention is a non-competitive system. This is demonstrated in Table 4, supra, where reland is shown not to compete. It is also noteworthy that unlike the release assay of the present invention, the competitive dissociation assays described by Cocola et al., Hinds et al., 1984 and Hinds et al., 1985, supra, are not shown to have significant advantage over other competitive methods of immunoassay. Although the present invention is not bound by any particular theory, we hypothesize that antibody binds to the release ligand via very low affinity interaction, and in the absence of higher affinity binding partners, antibody undergoes a conformational change to a metastable complex that is releasable. The complex may become too stable, as observed with conventional ligand conjugates. For example, N-isopropyl-norcotinine was designed to provide a bulky group at a non-immunologically critical site to allow release after formation of a stable complex.

Conclusion

We have developed an assay method utilizing the ability of receptors to assume an induced fit with a binding partner for which it has very low affinity, i.e. the release ligand, or reland. The release assay provides a stable preformed receptor:reland complex, which can be rapidly dissociated in the presence of analyte. The release system can be used in all immunoassay formats. The release assay has inherent advantages over conventional or associative assays:

1. By eliminating one step in the immune reaction, release saves time and steps and possible sources of error, thereby shortening assay time and simplifying assay techniques.
2. Release, i.e., dissociation, is inherently less subject to interference making it more accurate.
3. The ability to monitor all antibody in the assay reduces noise and makes a 1000–10,000-fold sensitivity range possible. This methodology, using more sensitive markers, extends the theoretical range both up and down from that available in conventional assay formats. Addition of more reactants does not lower sensitivity as in conventional immunoassays, but extends the upper range of sensitivity.
4. An important advantage of release is the mild conditions under which the dissociation occurs.
5. The large range, the positive correlation with presence of analyte, and the low noise of the system indicates that the release assay format can be used to screen for many analytes in one reaction mixture.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited throughout this specification, each of which is specifically incorporated herein by reference in its entirety.

What is claimed is:

1. A receptor-release ligand complex comprising a receptor bound to a monomeric or polymeric release ligand, wherein the receptor is capable of binding to an analyte, wherein the monomeric form of the release ligand binds to the receptor with an association constant of 1% or less of the association constant of the analyte for the receptor, and wherein the release ligand does not detectably compete with analyte for binding to the receptor.

2. The complex of claim 1 wherein the association constant of the monomeric release ligand for the receptor is less than or equal to about $10^5 M$.

3. The complex of claim 2 wherein the association constant of the monomeric release ligand is less than or equal to between $10^3$ and $10^5 M$.

4. The complex of claim 2 wherein the monomeric form of the release ligand binds to the receptor with an association constant of 0.2% or less of the association constant of the analyte for the receptor.

5. The complex of claim 2 wherein the release ligand is labelled with a label which becomes detectable after release of the release ligand from the receptor.

6. The complex of claim 2 wherein the receptor is an antibody or antibody fragment.

7. The complex of claim 2 wherein the receptor is immobilized.

8. The complex of claim 2 wherein the release ligand has a molecular weight of less than 5,000 Daltons.

9. A method for assaying for the presence or amount of an analyte in a sample comprising:
   a) contacting a receptor-release ligand complex comprising a receptor bound to a monomeric or polymeric release ligand, wherein the receptor is capable of binding to an analyte, wherein the monomeric form of the release ligand binds to the receptor with an association constant of 1% or less of the association constant of the analyte for the receptor, and wherein the release ligand does not detectably compete with analyte for binding to the receptor, with a sample suspected of containing the analyte to be detected; and
   b) detecting the dissociation of release ligand from the receptor complex as a measure of the presence or amount of analyte in the sample.

10. The method of claim 9 wherein the association constant of the monomeric release ligand for the receptor is less than or equal to about $10^5 M$.

11. The method of claim 9 wherein the association constant of the monomeric release ligand is less than or equal to between $10^3$ and $10^5 M$.

12. The method of claim 9 wherein the monomeric form of the release ligand binds to the receptor with an association constant of 0.2% or less of the association constant of the analyte for the receptor.

13. The method of claim 9 wherein the release ligand is labelled with a label detectable after release of the release ligand from the receptor, wherein the amount of analyte bound is proportional to the amount of label detected.

14. The method of claim 9 wherein the receptor is an antibody or antibody fragment.

15. The method of claim 9 wherein the receptor is immobilized.

16. The method of claim 9 wherein the release ligand has a molecular weight of less than 5,000 Daltons.

17. The method of claim 9 further comprising prior to step a) contacting the release ligand with the receptor in the absence of analyte.

18. An assay kit comprising a receptor-release ligand complex comprising a receptor bound to a monomeric or polymeric release ligand, wherein the receptor is capable of binding to an analyte, wherein the monomeric form of the release ligand binds to the receptor with an association constant of 1% or less of the association constant of the analyte for the receptor, and wherein the release ligand does not detectably compete with analyte for binding to the receptor, wherein the complex is immobilized onto a solid support phase, and detection means for indicating the presence or amount of receptor or release ligand upon dissociation from the release ligand-receptor complex.

19. The kit of claim 18 wherein the solid phase on which the complex is immobilized comprises a membrane which comprises a reaction field containing an indicator zone, wherein the receptor-release ligand complex is located in the reaction field, and at least part of the detection means is located in the indicator zone.

20. The kit of claim 18 comprising release ligand-receptor complexes for multiple analytes.

21. A method for obtaining a release ligand for use in an assay, wherein the release ligand forms a complex with a receptor which binds an analyte to be detected, comprising identifying compounds which are structurally similar to the analyte to be detected or which form a part of the analyte, screening the compounds to identify compounds binding to the receptor, and identifying the compounds which bind to the receptor in the presence and absence of analyte to select the compounds which bind to the receptor with an association constant of 1% or less of the association constant of the analyte for the receptor, and do not detectably compete with analyte for binding to the receptor.

22. The method of claim 21 wherein the compounds are prepared by synthesizing the analytes with one or more substitutions in the chemical structure.

23. The method of claim 21 wherein the compounds are prepared by isolating the epitope of the analyte bound by the receptor, and modifying the epitope to alter the binding properties.

* * * * *